(12) United States Patent
Khait et al.

(10) Patent No.: US 9,526,080 B2
(45) Date of Patent: Dec. 20, 2016

(54) SYSTEMS AND METHODS FOR SYNCHRONIZING BETWEEN AN IN-VIVO DEVICE AND A LOCALIZATION SYSTEM

(75) Inventors: Semion Khait, Tiberias (IL); Oren Rosenberg, Kiryat Ono (IL)

(73) Assignee: GIVEN IMAGING LTD., Yoqneam (IL)

( * ) Notice: Subject to any disclaimer, the term of this patent is extended or adjusted under 35 U.S.C. 154(b) by 378 days.

(21) Appl. No.: 14/005,338

(22) PCT Filed: Mar. 18, 2012

(86) PCT No.: PCT/IL2012/050096
§ 371 (c)(1),
(2), (4) Date: Sep. 16, 2013

(87) PCT Pub. No.: WO2012/127469
PCT Pub. Date: Sep. 27, 2012

(65) Prior Publication Data
US 2014/0003418 A1    Jan. 2, 2014

Related U.S. Application Data

(60) Provisional application No. 61/466,145, filed on Mar. 22, 2011.

(51) Int. Cl.
*A61B 19/00* (2006.01)
*H04W 56/00* (2009.01)
(Continued)

(52) U.S. Cl.
CPC ...... *H04W 56/0015* (2013.01); *A61B 1/00016* (2013.01); *A61B 1/041* (2013.01);
(Continued)

(58) Field of Classification Search
CPC .................. G01S 11/08; H04W 64/00
(Continued)

(56) References Cited

U.S. PATENT DOCUMENTS

| | | | | |
|---|---|---|---|---|
| 6,493,649 | B1 * | 12/2002 | Jones | G01S 5/186 367/99 |
| 7,032,600 | B2 * | 4/2006 | Fukuda | A61B 1/041 128/899 |

(Continued)

FOREIGN PATENT DOCUMENTS

| | | |
|---|---|---|
| EP | 1440659 | 7/2004 |
| EP | 2177159 | 4/2010 |

(Continued)

OTHER PUBLICATIONS

US 7,392,808, 7/2008, Minai et al. (withdrawn).
(Continued)

*Primary Examiner* — Mohamed Kamara
*Assistant Examiner* — Will Lin
(74) *Attorney, Agent, or Firm* — Pearl Cohen Zedek Latzer Baratz LLP

(57) ABSTRACT

An in-vivo device may allocate a sensing window in a work cycle for sensing and processing localization signals to determine the location/orientation of the in-vivo device. The in-vivo device may use a timing unit to schedule transmission of data frames and the sensing of the localization signals relative to a reference time embedded in work cycles. The timing unit may produce a clock signal based on which the in-vivo device may measure time specifics, which define the sensing window, relative to the reference time. A receiver may use data embedded in data frames to restore the clock signal and the reference time, and, from them, and using identical or similar time specifics, generate a synchronization signal for a localization signals source (LSS) to enable
(Continued)

the LSS to generate localization signals in synchronization with the sensing windows.

20 Claims, 15 Drawing Sheets

(51) Int. Cl.
    *A61B 5/06*         (2006.01)
    *A61B 5/00*         (2006.01)
    *A61B 1/00*         (2006.01)
    *A61B 1/04*         (2006.01)
    *A61B 5/07*         (2006.01)
    *A61N 2/00*         (2006.01)

(52) U.S. Cl.
    CPC .............. *A61B 5/061* (2013.01); *A61B 5/073* (2013.01); *A61B 5/6861* (2013.01); *A61B 5/7285* (2013.01)

(58) Field of Classification Search
    USPC .................................................. 370/350, 324
    See application file for complete search history.

(56) References Cited

U.S. PATENT DOCUMENTS

| | | |
|---|---|---|
| 7,398,117 B2 | 7/2008 | Minai |
| 7,509,158 B2 | 3/2009 | Minai |
| 7,523,756 B2 | 4/2009 | Minai |
| 7,536,217 B2 | 5/2009 | Minai |
| 7,580,739 B2 | 8/2009 | Minai |
| 7,603,160 B2 | 10/2009 | Suzuki |
| 7,686,757 B2 | 3/2010 | Minai |
| 8,396,563 B2* | 3/2013 | Reinke ............... A61N 1/37288 607/2 |
| 2005/0143649 A1 | 6/2005 | Minai |
| 2005/0187479 A1 | 8/2005 | Graumann |
| 2005/0200351 A1 | 9/2005 | Shimizu |
| 2007/0038063 A1 | 2/2007 | Kuth et al. |
| 2007/0167743 A1 | 7/2007 | Honda et al. |
| 2007/0244388 A1 | 10/2007 | Sato et al. |
| 2007/0252893 A1 | 11/2007 | Shigemori |
| 2007/0255087 A1* | 11/2007 | Minai ................ A61B 1/041 600/12 |
| 2008/0039688 A1 | 2/2008 | Minal et al. |
| 2008/0200760 A1 | 8/2008 | Minai et al. |
| 2008/0262303 A1* | 10/2008 | Minai ................ A61B 1/041 600/117 |
| 2009/0018434 A1 | 1/2009 | Kimura et al. |
| 2009/0131784 A1 | 5/2009 | Betesh |
| 2010/0060472 A1 | 3/2010 | Kimura et al. |
| 2010/0073185 A1 | 3/2010 | Uchiyama et al. |

FOREIGN PATENT DOCUMENTS

| | | |
|---|---|---|
| JP | 2005257301 | 9/2005 |
| JP | 2006346007 | 12/2006 |
| JP | 2008011913 | 1/2008 |
| JP | 2009 000401 | 1/2009 |
| WO | WO 2007/110270 | 10/2007 |
| WO | WO 2007/110278 | 10/2007 |
| WO | WO 2007/113055 | 10/2007 |
| WO | WO 2009/027191 | 3/2009 |
| WO | WO 2009/031456 | 3/2009 |
| WO | WO 2009/041524 | 4/2009 |
| WO | WO 2009/083409 | 7/2009 |
| WO | WO2009/107892 | 9/2009 |

OTHER PUBLICATIONS

International Search Report of Application No. PCT/IL2012/050096 mailed on Aug. 24, 2012.

European Search Report of Application No. 12761307.3 dated Aug. 18, 2016.

* cited by examiner

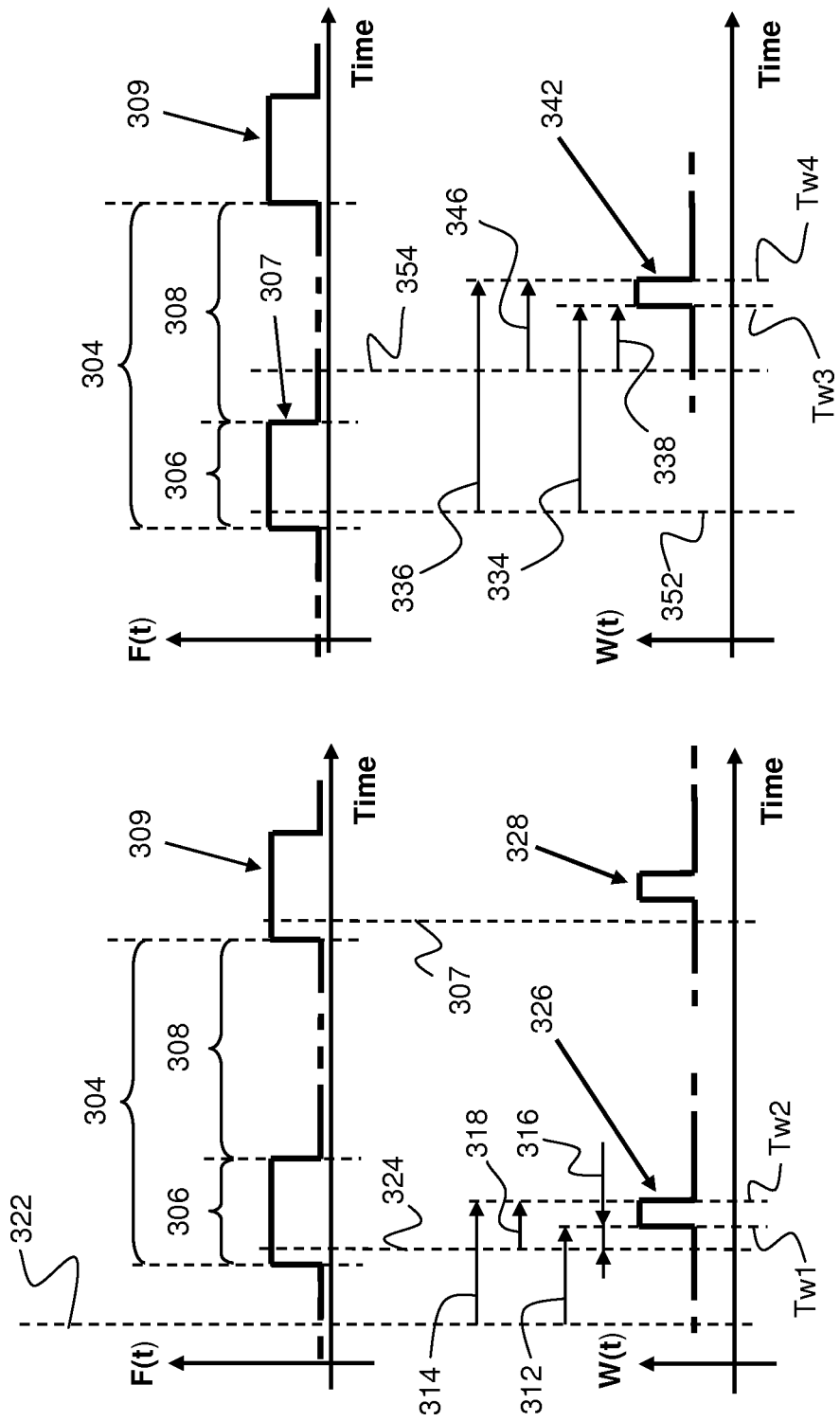

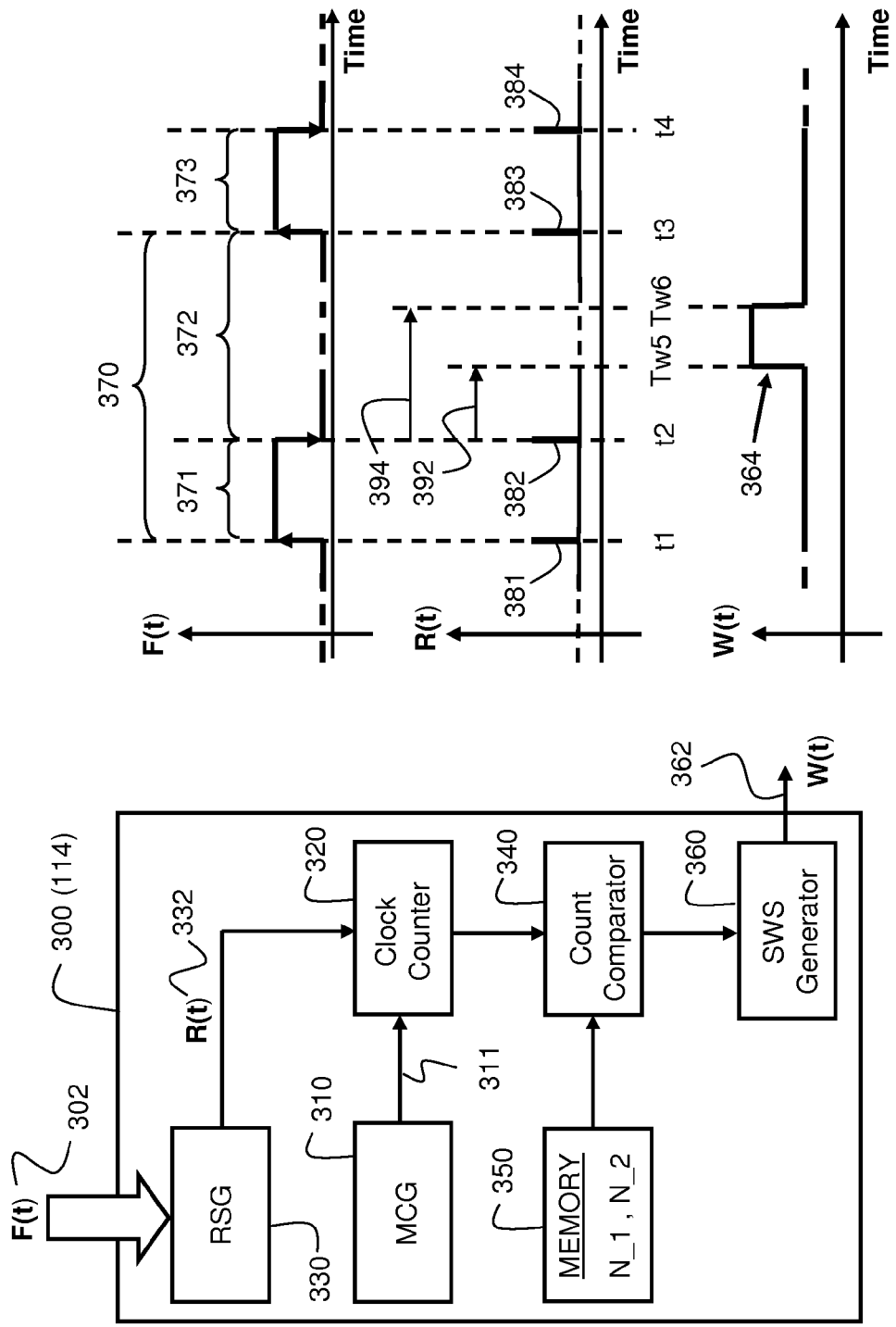

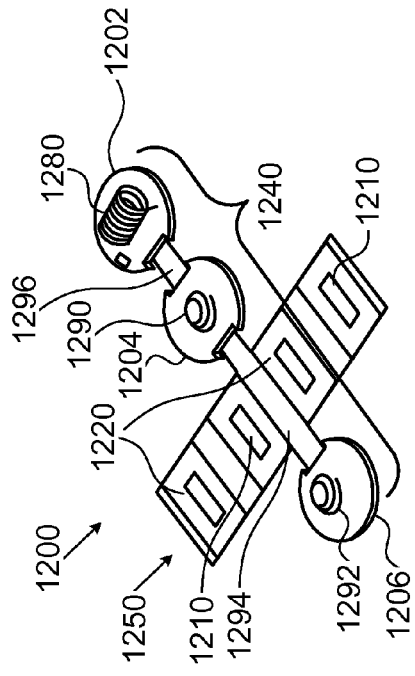
FIG. 12B
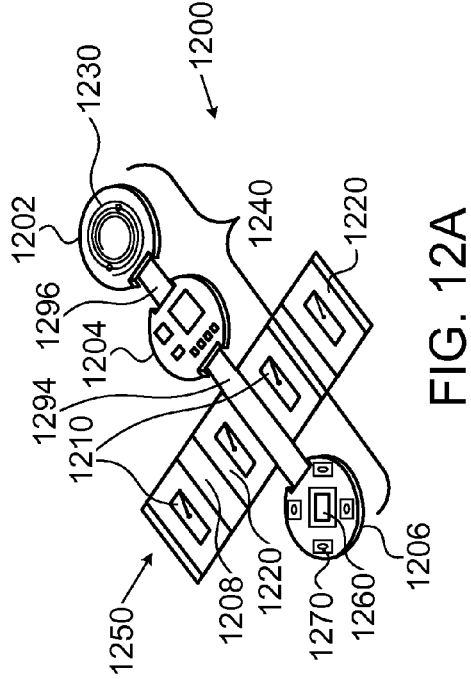
FIG. 12A
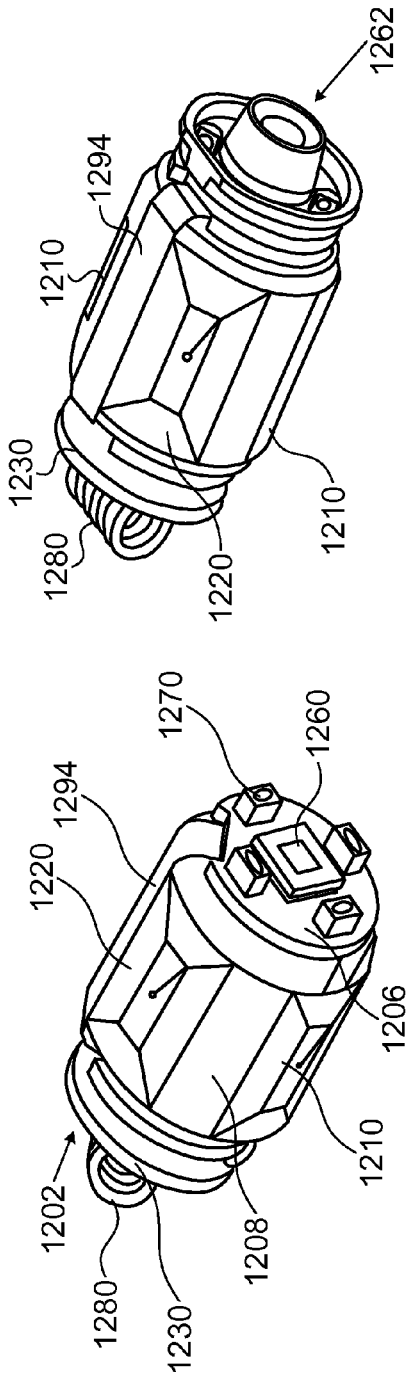
FIG. 12D
FIG. 12C

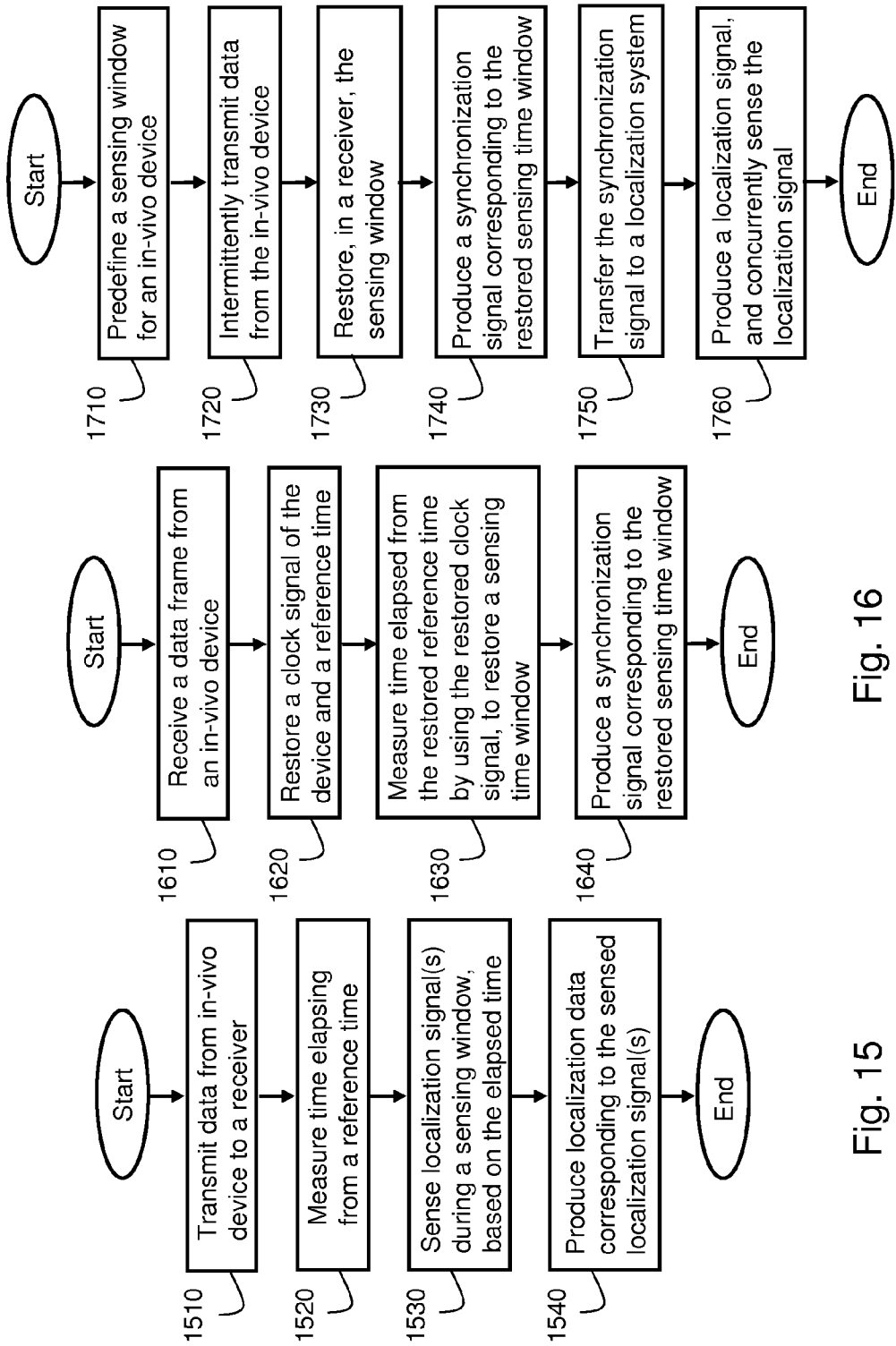

SYSTEMS AND METHODS FOR SYNCHRONIZING BETWEEN AN IN-VIVO DEVICE AND A LOCALIZATION SYSTEM

CROSS-REFERENCE TO RELATED APPLICATIONS

This application is a National Phase Application of PCT International Application No. PCT/IL/2012/050096, International Filing Date Mar. 18, 2012, entitled Systems and Methods for Synchronizing between an In-Vivo Device and a Localization System, published on Sep. 27, 2012 as International Publication Number WO 2012/127469 claiming priority of claiming priority of U.S. Provisional Patent Application No. 61/466,145, filed Mar. 22, 2011, which are incorporated herein by reference in its entirety.

FIELD OF THE INVENTION

The present invention generally relates to an in-vivo system and more specifically to a synchronization method for synchronizing between an in-vivo device and an in-vivo device localizing system, and to an in-vivo system and localization signal system using the synchronization method.

BACKGROUND

In-vivo measuring systems are known in the art. Some in-vivo devices/systems that traverse the gastrointestinal (GI) system may include one or more imaging sensors, for imaging (e.g., capturing images of) the interior of the GI system, and/or sensors of other types. In-vivo devices may traverse the GI system by being pushed through the GI system by peristaltic force exerted by the digestive system, or by being maneuvered (e.g., magnetically). Some applications require knowing the current location and/or current orientation of the involved in-vivo device. For example, in order to magnetically maneuver an in-vivo device, for example in the GI system, the magnetic maneuvering system has to know the current location/orientation (and the target location/orientation) of the in-vivo device in order to generate the correct steering magnetic fields.

Conventional localization systems use various techniques to detect the location and/or orientation of in-vivo devices. In some systems, the in-vivo device includes a magnet for producing a constant magnetic field that is sensed outside the in-vivo device. For example, U.S. Pat. No. 7,392,808 discloses a system for detecting the location of an in-vivo device that includes a magnetic field generator that generates a constant magnetic field that is sensed by external magnetic field detectors. Due to the limited space in in-vivo devices, inclusion of a magnet in them is undesirable.

In other localization systems, such as in the system disclosed in U.S. Patent application number 2009/0018434, the in-vivo device includes a resonant circuit. Measuring the influence of the resonant circuit on an external magnetic field enables to locate the in-vivo device. Such systems, which typically use an external magnetic field generator and an external magnetic field detector, require that the patient whose GI system is monitored be positioned at a certain location in-between the magnetic field generator and the external magnetic field detector.

In other localization systems the in-vivo device contains magnetic field sensing coils, and the external magnetic field generator generates an alternating magnetic field continuously, which is undesirable for various reasons. One reason is that a constant alternating magnetic field may interfere with other functions of the device. Another reason is that the in-vivo device has to continuously allocate resources to process the signals induced in the magnetic sensing coils, rather than being able to use these resources for other tasks as well.

Advanced maneuvering systems use alternating current ("AC") magnetic fields and direct current ("DC") magnetic fields to maneuver devices in vivo. However, an advanced maneuvering system and a conventional localization system cannot coexist, for example, because the external maneuvering AC magnetic field may have a negative side effect on the readout of the localization sensing coil of the in-vivo device, and the external AC localization signal may have a negative side effect on the maneuvering force that maneuvers the in-vivo device. If an in-vivo device includes a 'localization' magnet (as opposed to a 'maneuverable' magnet), for example as per the localization system disclosed in U.S. Pat. No. 7,392,808, the external maneuvering DC magnetic field may apply an undesired maneuvering force on the in-vivo device's localization magnet. If an in-vivo device includes an LC circuit, for example as per the localization system disclosed in US 2009/0018434, localizing and maneuvering the in-vivo device may suffer from at least some of the aforesaid deficiencies.

For at least the reasons set forth above, conventional localization systems impede usage of advanced maneuvering systems. Therefore, it would be beneficial to have a method that would enable a magnetic maneuvering system to steer an in-vivo device and a magnetic localization system to locate the in-vivo device without the two systems interfering with one another. In addition, since an in-vivo device typically performs various tasks (e.g., imaging the GI system, processing various types of data, storing/retrieving data in/from its memory, transmitting sensory data, receiving commands, etc.) that are timed internally, it would also be beneficial to synchronize between transmission of localization signals by a localization system and sensing of these signals by the in-vivo device.

SUMMARY

An electromagnetic field sensing time window ("sensing window" for short) may be allocated in a work cycle of the in-vivo device for sensing electromagnetic localization signals, and for processing the sensed signals. The in-vivo device may operate according to the work cycle. A "work cycle" may be a cycle or repeated time period, divided into time slots or periods, that includes a transmission period during which the in-vivo device transmits data (e.g., data frame; e.g., image frame), for example to a data recorder, via a first communication channel, and an idle period during which the in-vivo device does not transmit data via the first communication channel (but it may transmit data via a second communication channel or be occupied executing internal tasks). Time specifics (e.g., start time, duration, termination time) that may define the sensing window may be defined such that the sensing window is wide enough (e.g., encompass a long enough time period) to enable the in-vivo device to sense as many localization signals as required to determine the location and/or orientation of the in-vivo device, and narrow enough and located in the work cycle such that it would not interfere with other activities that the in-vivo device may be involved in. The sensing window may be divided to, or include, n (n=1, 2, 3, . . . ,) sensing sub-windows to enable the in-vivo device to sense, for example, n localization signals during each sensing window, and additional time specifics may include time information related to the sensing sub-windows as well. In one embodiment, n=3 to enable the in-vivo device to sense three localization signals that may be associated, for example, with an X,Y,Z coordinates system. One or more sensing sub-windows may additionally be used to sense orientation signals for determining the spatial orientation of the in-vivo device. "Localization signal" and "orientation signal" are hereinafter collectively referred to herein as "localization signal" and "sensing signal". Each particular localization signal may be sensed during a particular sensing sub-window which the in-vivo device may allocate/reserve for it.

In one embodiment, the sensing window may reside, be within the time period defined by, or may occur, in idle periods. In another embodiment, the sensing window may reside in transmission periods. In one embodiment, the in-vivo device may transmit localization data that represent sensed electromagnetic signals during a transmission period. In another embodiment, the in-vivo device may transmit the localization data by using a second (e.g., telemetry) communication channel that is disassociated from the first communication channel.

The in-vivo device may schedule (e.g., temporally locate) the sensing of the localization signals in work cycles (as per the time specifics defined for the sensing window and/or for the sensing sub-windows) by using an internal timing mechanism. The in-vivo device may schedule the sensing of the localization signals relative to an internal reference time whose temporal location in each work cycle may be fixed. The time specifics defining the sensing window (and the sensing sub-windows, if they exist) may be measured relative to the internal reference time, which, in general, may be preset to be at any time point within the work cycles. In one embodiment, the internal reference time may be preset to be at, or near, the beginning of a transmission period. In another embodiment, the internal reference time may be preset to be at, or near, the end of a transmission period. In yet another embodiment, the internal reference time may be preset to be at a time point within the transmission period of working cycles. In still another embodiment, the internal reference time may be preset to be at a time point in the idle period of working cycles. The timing mechanism may include a master clock to produce a (master) clock signal for timing data bits, and based on the master clock signal the in-vivo device may measure time elapsing from the preset reference time, in order to determine when the elapsed time matches any of the time specifics, and thus when the elapsing time overlaps with the sensing window. Time specifics of the sensing window may be constant or they may be adjusted or varied, for example contingent on a rate at which the in-vivo device transmits data (e.g., image data).

The data recorder may use, for example, a specific data bit (e.g., data bit number 1000 in a data frame) or a group of data bits, or any suitable signal, that it receives from the in-vivo device to restore or generate the in-vivo device's internal reference time. The data recorder may also use, for example, a group or series of data bits it receives from the in-vivo device to restore the in-vivo device's master clock signal. The data recorder may use the restored reference time and the restored master clock signal, in conjunction with time specifics that are identical or similar (e.g., adjusted) to the time specifics used internally by the in-vivo device to generate a synchronization signal for a localization signals source ("LSS"). The LSS may use the synchronization signal to generate localization signals in synchronization with the time specifics defining the sensing window and/or sensing sub-windows.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIGS. 3A and 3B show sensing windows according to example embodiments;

FIG. 3C shows a timing unit according to an example embodiment;

FIG. 3D shows a timing diagram associated with the timing unit of FIG. 3C;

FIGS. 12A and 12B depict a printed circuit board ("PCB") of an in-vivo device that is configured to sense localization signals according to an example embodiment;

FIGS. 12C and 12D depict the PCB of FIGS. 12A-12B folded/introverted according to an example embodiment;

FIG. 15 shows a method for timing internal sensing, by an in-vivo device, of externally generated localization signals according to an example embodiment;

FIG. 16 shows a method for synchronizing between sensing of localization signals by an in-vivo device and generation of the localization signals by an external localization signals source according to another example embodiment; and FIG. 17 shows a method for synchronizing generation of a localization signal to sensing of the localization signal in an in-vivo device according to another example embodiment.

DETAILED DESCRIPTION

Figure 1:
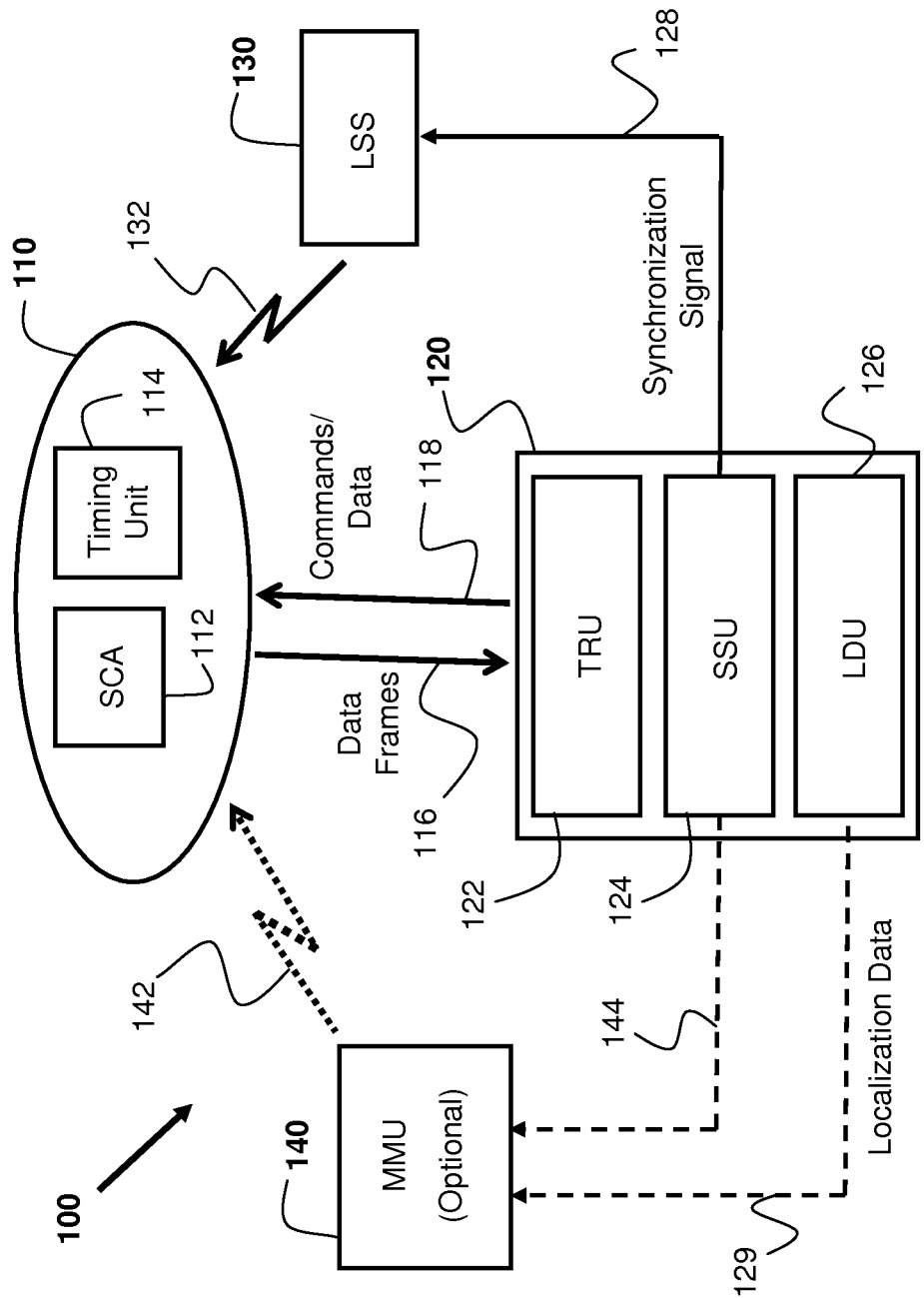
FIG. 1 is a block diagram of a localization system for localizing an in-vivo device according to an example embodiment.

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining," "inferring", "deducing", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not constrained to a particular order or sequence. Additionally, some of the described method embodiments or elements thereof can occur or be performed at the same point in time.

In general, an in-vivo device operating with an in-vivo device localization system may be capable, among other things, of: (i) transferring data frames to (and in some embodiments exchanging data with) the data recorder with which it operates, (ii) sensing localization signals (e.g., electromagnetic localization signals) that are generated by an external system, and (iii) processing the localization signals and transmitting consequent localization data to the data recorder. The localization data transmitted by or from the in-vivo device may represent the raw signal(s) that are induced in the in-vivo device by localization signals, and thus it may have to be processed by an external system in order to determine the location of the in-vivo device. Alternatively, the raw signals may be processed internally (by the in-vivo device), and the consequent localization data transmitted by or from the in-vivo device may represent the location (and/or orientation) of the in-vivo device. The data recorder may be capable, among other things, of: (i) receiving the data frames from the in-vivo device, and (ii) using data frames to generate a synchronization signal in order to synchronize between the system generating the localization signals and the in-vivo device sensing the localization signals.

In one embodiment the system generating the localization signal may transmit localization signals at specific times and for specific time periods which are preset for (and governed by) the in-vivo device because localization signals are to be transmitted to the in-vivo device only during time slots that the in-vivo device allocates or reserves for sensing this type of signals. This type of synchronization helps ensure that localization signals are transmitted to the in-vivo device only when the in-vivo device is ready to receive and process them. In general, a time slot (herein referred to as the "sensing window") may be allocated within each work cycle (e.g., within the transmission period of each work cycle, or within the idle period of each work cycle) or within selected work cycles according to which the in-vivo device operates. The sensing window may be used to sense localization signals that originate from an external localization signals source (LSS).

The time specifics (e.g., timing and width or duration) of the sensing window and/or the time specifics of sensing sub-windows may be predetermined or chosen in advance after taking into account various time constraints of the in-vivo device, such as a need to allocate a time slot for sensing a physical parameter in vivo (e.g., for imaging objects, sensing pH, etc.), another time slot for receiving instructions and/or data from an external source, another time slot for processing the instructions and/or data received from the external source, etc.

A timing mechanism in the in-vivo device, which may predominate the timing of various processes, tasks, etc. of the in-vivo device, may measure time (e.g., by counting clock pulses) in order to identify a start time (Ts) and a termination time (Tt) of the sensing window. During a sensing window the in-vivo device may switch to or enter, and temporarily remain in, a sensing mode. During the sensing mode the in-vivo device may sense one or more localization signals during, for example, the respective sensing sub-windows. When the sensing window elapses, the in-vivo device may exit the sensing mode, for example to commence or resume other tasks. Assuming a 3-dimensional location of the in-vivo device is determined by using the X,Y,Z coordinates system, a localization signal associated with the X-axis may be generated by an external system and sensed internally by the in-vivo device during a sensing sub-window which is allocated for it, and other localization signals may likewise be generated and sensed for the Y-axis and for the Z-axis.

The external localization signals source (LSS) that generates the localization signals may be subjected to various constraints with regard to the timing of the generation of the localization signals. For example, generating the localization signals while the in-vivo device is transmitting data (e.g., image data) may detrimentally affect the transmission and/or the reception of the data by a receiver (e.g., data recorder). Therefore, it may be beneficial to generate the localization signals while the in-vivo device is not transmitting data. However, as discussed above, since during idle periods the in-vivo device may still be busy doing other internal activities (e.g., receiving data, processing data), a synchronization signal is transferred to the localization signals source (LSS) to thereby indicate to the LSS the sensing window and/or sensing sub-windows that the in-vivo device has allocated for localization signals. The synchronization signal may be produced externally to the in-vivo device (e.g., by the data recorder) based on the in-vivo device's restored timing mechanism (e.g., restored or generated reference time and restored master clock signal). Synchronizing between the in-vivo device and the LSS, therefore, means that the LSS generates the localization signals during a sensing window (and sensing sub-windows) whose time specifics have been suited to, or governed or dictated by, the in-vivo device.

The way the in-vivo device's timing mechanism is restored by the data recorder (for example) and the way the consequent synchronization signal is used by the LSS are described below. Briefly, clock pulses originating from a master clock of the in-vivo device may be used to count time units (a time 'unit' may equal to, e.g., 1 microsecond) relative to a reference time (e.g., beginning of data transmission from the in-vivo device, end of data transmission from the in-vivo device, or a particular data bit in a transmitted data frame, or a particular pulse count during an idle period, etc.). Any data bit or group of data bits (e.g., prefix data, suffix data, etc.) that is/are contained in a data frame that is transmitted by the in-vivo device may be used by a receiver (e.g., data recorder) to restore the clock pulses originating from the in-vivo device. The restored clock pulses may be used by the receiver to count time by using the same time units and relative to the same reference time. Based on the time counting, the LSS may be caused (e.g., by the data recorder) to start transmitting a localization signal when the time count has a first value; e.g., Count1, and terminate the transmission when the time count has a second value, e.g., Count2 (where Count2>Count1). ('Count1' may designate or represent the start time of the pertinent sensing window, and 'Count2' may designate or represent the termination time of that sensing window.) The in-vivo device may enter, transition to, or enable a sensing mode when the time count equals, for example, count value Count1, and exit or disable the sensing mode when the time count equals, for example, count value Count2. During the sensing mode, the in-vivo device may, during the time periods of the sensing window(s), sense and process localization signal(s).

FIG. 1 is a block diagram of a localization system 100 for localizing an in-vivo device according to an example embodiment. Localization system 100 may include an in-vivo device 110, a data recorder 120, and a localization signals source ("LSS") 130. In-vivo device 110 may be configured to sense a physical parameter in vivo. Temperature, pH, and impedance are example physical parameters. In-vivo device 110 may sense other physical parameters and/or be capable of performing various surgical operations in vivo. In-vivo device 110 may capture images (e.g., take pictures) in vivo (e.g., of the GI system). In-vivo device 110 may include a transmitter for transmitting data, for example to data recorder 120, which is related to sensed physical parameter and/or related to or represent captured images.

In-vivo device 110 may also include a sensing coils assembly ("SCA") 112 for sensing localization signals generated by an external localization system, for example by localization signals source (LSS) 130. SCA 112 may include one electromagnetic sensing coil for sensing an electromagnetic field, or more than one electromagnetic sensing coil that may be mutually perpendicular. Each electromagnetic sensing coil may be used to sense an electromagnetic field in a different direction/orientation. For example, one coil may be used to sense an electromagnetic field in the 'X' direction or in the Y-Z plane, another coil may be used to sense an electromagnetic field in the 'Y' direction or in the X-Z plane, etc. Each localization signal generated by localization signals source (LSS) 130 may induce an electromotive force ("EMF") signal on one or more of the electromagnetic sensing coils of SCA 112, and the current location, and optionally the current orientation, of in-vivo device 110 may be determined based on the EMF signal sensed by the coils of SCA 112. Example electromagnetic sensing coils are shown in FIGS. 12A through 12D, which are described below. In-vivo device 110 may also include a timing unit 114 for scheduling the time specifics (e.g., starting time and duration) of the sensing window during which SCA 112 may be activated and the EMF signals measured. An example timing unit is shown in FIG. 3C, which is described below.

Data recorder 120 may include, among other things (e.g., receiver, data frame parser, data storage unit, processor, etc.), a timing restoration unit ("TRU") 122, a synchronization signal unit ("SSU") 124, and a localization data unit ("LDU") 126. Data recorder 120 may include a receiver (not shown in FIG. 1) for receiving data frames 116 from in-vivo device 110. Data recorder 120 may also include a transmitter for transmitting commands 118 to in-vivo device 110. Data recorder 120 may transmit a command to in-vivo device 110, for example, to change a mode of operation (e.g., an image capturing rate of an imager of the in-vivo device), or to update a parameter of the in-vivo device, etc.

Figure 4:
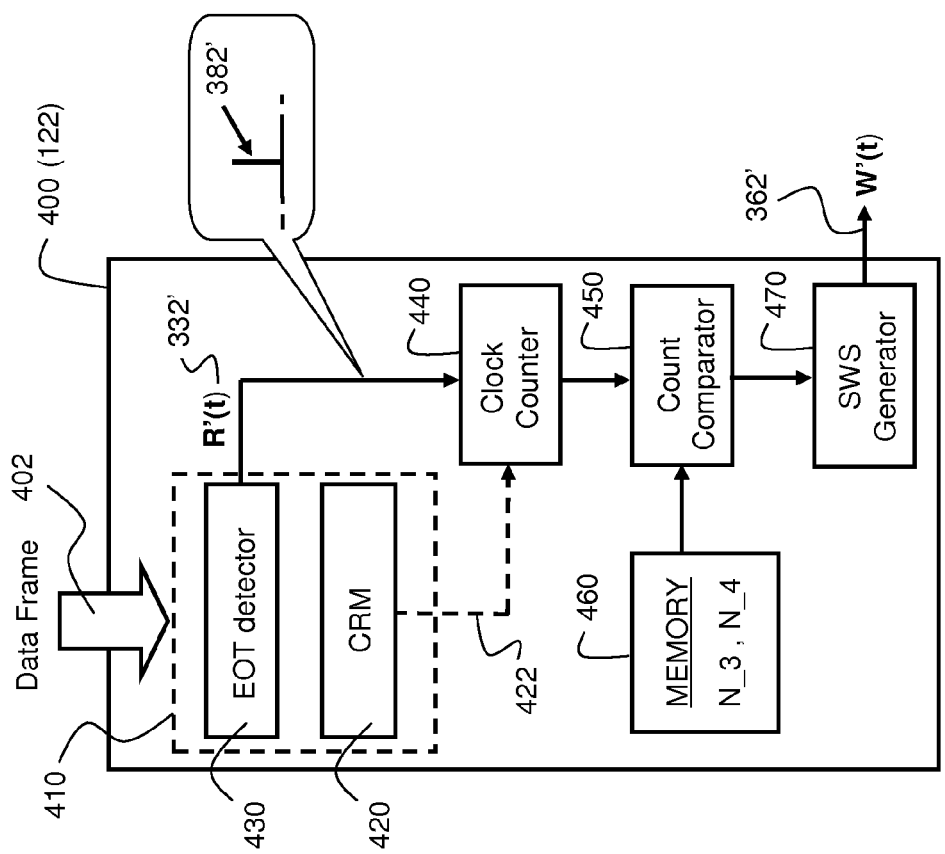
FIG. 4 shows a timing restoration unit according to an example embodiment.

As explained above, a data frame transmitted by in-vivo device 110 and received by data recorder 120 may include a data bit or a group of data bits that may facilitate generation, reconstruction or restoration, for example by TRU 122, of the clock pulses and the time reference originating from timing unit 114 and used by in-vivo device 110. TRU 122 may use the restored clock pulses and the reference time to find a time period that overlaps or coincides with the time specifics of the sensing window(s) used by in-vivo device 110. For example, TRU 122 may count restored clock pulses relative to a reference time in each or selected work cycles of the in-vivo device in order to measure the time elapsing, in the work cycle, from the pertinent reference time. An example timing restoration unit (TRU) is shown in FIG. 4, which is described below. In general, any $i^{th}$ data bit in a data frame that is transmitted during a particular work cycle may be used or serve as a reference time for that work cycle (e.g., the time of transmission of that bit may be used as a reference time), and the same $i^{th}$ data bit may be used by both the in-vivo device and the data recorder as a common reference time. For example, it may be predetermined, for example, that the $100^{th}$ bit in each data frame (or the time the $100^{th}$ bit is transmitted) is used as the reference time during the pertinent work cycle.

Concurrently to the restoration of the in-vivo device's clock signal and reference time by the timing restoration unit (TRU) 122, synchronization signal unit (SSU) 124 may produce a synchronization signal 128 that complies with the time specifics of the sensing window(s), and may transfer synchronization signal 128 to localization signals source (LSS) 130, for example via a communication cable or wirelessly. Synchronization signal 128 enables LSS 130 to correctly time the generation or creation of one or more localization signals (in the form of electromagnetic field(s)). For example, LSS 130 may generate an electromagnetic field 132 at a time and for a duration set forth by, or complying with, synchronization signal 128, and therefore, in compliance with the restored sensing window(s), and therefore in compliance with the sensing window(s) originally used by in-vivo device 110. Since the sensing window(s), which may be used by in-vivo device 110 during each or selected work cycles, and the restored sensing window(s) used by data recorder 120 temporally match (within an acceptable margin), LSS 130 generates and transmits localization signal 132 exactly in the time slot(s) during which in-vivo device 110 uses sensing coils assembly (SCA) 112 to sense the induced EMF signals and allocates the resources required for processing the induced EMF signals.

As a result of in-vivo device 110 sensing the induced EMF signals during a particular work cycle, the in-vivo device 110 may embed data representative of the sensed EMF signals in a data frame that is transmitted (e.g., to a data recorder) during a transmission period, for example, of a work cycle that follows the particular work cycle. Data that represent the raw EMF signals, and any variant, manipulation, or derivative of such data (e.g., data representing the actual location of the in-vivo device) is referred to herein as "localization data" and "sensing data". As defined above, "localization data" may also refer to data that is sensed by the in-vivo device and which represents the orientation of the in-vivo device or allows the device to determine the orientation. Alternatively, localization data may be transmitted (e.g., to a data recorder) not by using the communication channel via which frames are transmitted, but by using a separate communication channel. Using a separate communication channel to transmit localization data may enable transmission of large amount of localization data.

Localization data unit (LDU) 126 may include or use a processor and other components and units that are required to interpret, calculate, deduce, infer, or otherwise determine the current position, and, optionally, also the current orientation, of in-vivo device 110 from the localization data. After LDU 126 determines the location/orientation of the in-vivo device, LDU 126 may transfer corresponding localization data 129 to another computing system. Localization data 129 may include data that represents the current location of in-vivo device 110, or the current orientation of in-vivo device 110, or both location and orientation of in-vivo device 110. The other computing system may, for example, display the location/orientation data (whether the raw data or a processed version thereof), and/or it may use past and current location/orientation data to display the route traversed by the in-vivo device and/or a point on a route representative of the GI system, and/or it may use localization data 129 to maneuver, guide or steer in-vivo device 110.

Figure 2:
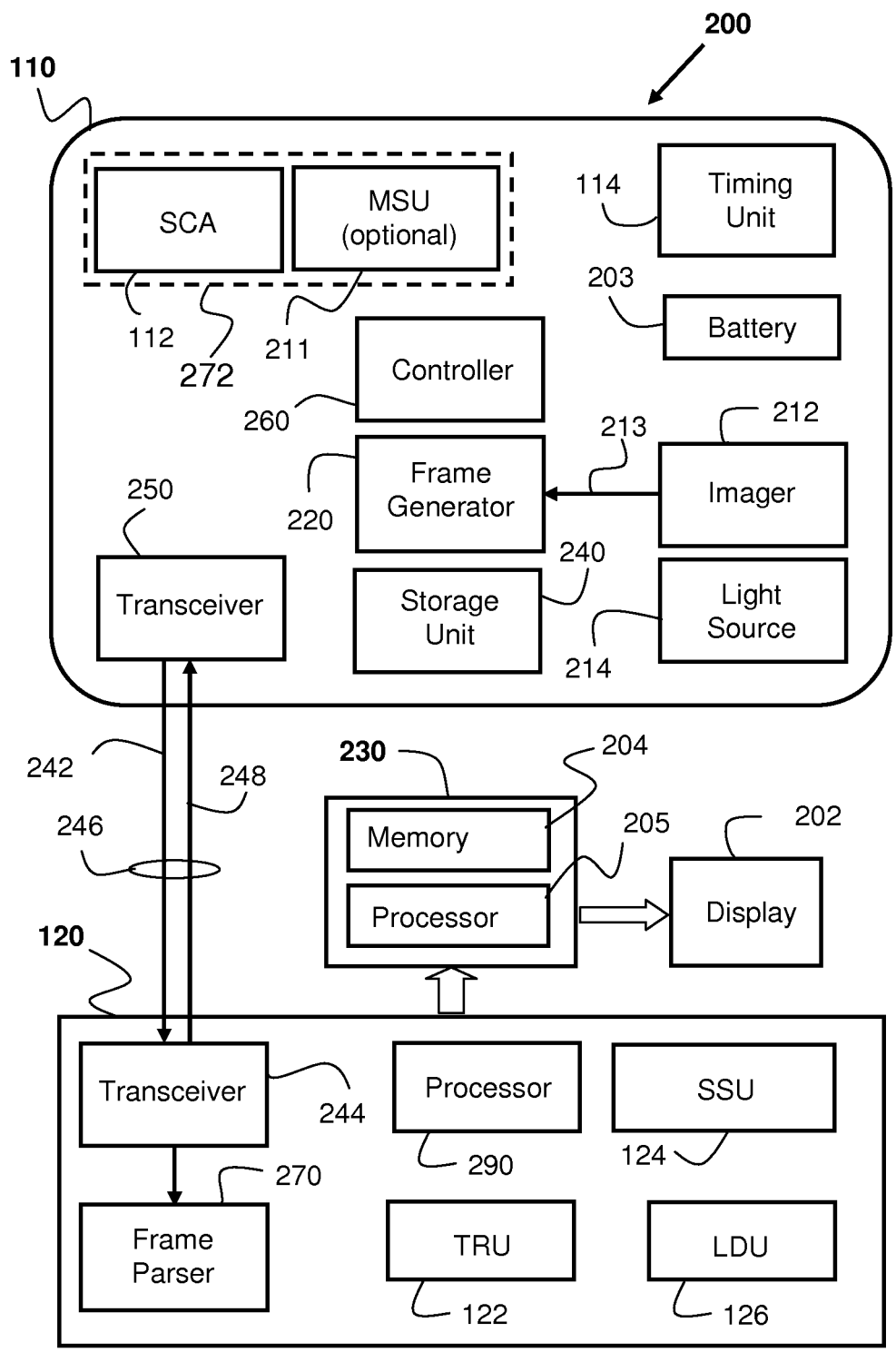
FIG. 2 shows an in-vivo imaging system according to an example embodiment.

Localization system 100 may also include a magnetic maneuvering unit ("MMU") 140 for maneuvering in-vivo device 110, and. LDU 126 may transfer position/orientation data 129 to MMU 140 in order for MMU 140 to use position/orientation data 129 as a feedback to generate a maneuvering magnetic field 142 to guide, steer, or maneuver, in-vivo device 110 to a new, target or desired location and/or to a new, target or desired orientation. That is, knowing the current location/position of in-vivo device 110 (e.g., from location/position data 129), MMU 140 may generate an electromagnetic signal 142 to maneuver in-vivo device 110 to a required, or target, location or orientation. SCA 112 may be part of a magnetic steering unit ("MSU"). (An MSU is shown in FIG. 2 at 211.) The MSU may include, for example, permanent magnets and Eddy current element(s). The permanent magnets and Eddy current element(s) of the MSU may interact with electromagnetic signal 142 to produce magnetic forces and torques capable of steering the in-vivo device. MMU 140 may control the steering of in-vivo device 110 based, for example, on location/orientation signals that are provided by LDU 126 (e.g., position/orientation data 129). An example MSU is depicted, for example, in FIG. 13A, which is described below.

The operation of MMU 140 may be synchronized to the operation of LSS 130 in order to ensure that MMU 140 and LSS 130 do not respectively generate maneuvering signal 142 and localization signal 132 at the same time. Operation of MMU 140 may be synchronized to the operation of LSS 130 also to ensure that MMU 140 generates a position (or orientation) correction signal 142 that is based on up to date localization/orientation data. SSU 124 may send a synchronization signal 144 to MMU 140 in order to synchronize between MMU 140 and LSS 130. Synchronization signal 144 may be identical to synchronization signal 128 or a manipulation or derivative thereof. Synchronization signal 144 may cause MMU 140 to generate, for each work cycle of the in-vivo device, a signal 142 in the form of a short maneuvering signal (a 'maneuvering burst'), or a series of maneuvering bursts, shortly after a sensing window is terminated, provided that MMU 140 receives the localization data for the sensing window.

FIG. 2 shows an in-vivo imaging system 200 according to an example embodiment. While FIG. 1 references an in-vivo device (in-vivo device 110) that transmits data frames that may be related to or include any type of sensory data (e.g., pH data), FIG. 2 shows in-vivo device 110 with an imager as an example sensor, in which case in-vivo device 110 may be referred to as an "in-vivo imaging device" or an "in-vivo imager", and frames transmitted by or from in-vivo device 110 may be referred to as "image frames" (although image frames may include also other types of data, including localization data and/or other types of sensory data). In-vivo imaging system 200 includes in-vivo imager 110, data recorder 120, a user workstation 230, which may be, for example, a workstation or personal computer, and a display 202 for displaying, for example, images and/or a video clip or moving image stream which is produced from images, and for displaying the location and/or orientation of the in-vivo device, etc.

An in-vivo imaging device may have one or more imagers. By way of example, in-vivo imager 110 includes one imager (e.g., imager 212) (numbers of imagers other than one or two may be used, with suitable modifications to the methods discussed herein). In-vivo imager 110 may also include a light/illumination source 214 for illuminating a GI section to be imaged, a frame generator 220 for producing an image frame for captured images, a controller 260, a storage unit 240 for storing data, a transmitter or transceiver 250 for transmitting images frames and, optionally, for receiving data and/or commands from data recorder 120, and an electrical power source 203 for powering these components and circuits. Power source 203 may include a charge storing device (e.g., one or more batteries, which may be rechargeable or not) with an electrical circuit that jointly facilitates transfer of electrical power from an external power source to the in-vivo device through electromagnetic induction.

Timing unit 114 may include a timing mechanism (e.g., clock generator) to generate a clock signal to time a work cycle of the in-vivo device. Within the work cycle may be defined a reference time. Transmitter 250 may transmit, within the work cycle, a data frame to a receiver (e.g., data recorder 120). The data frame may contain or include data facilitating restoration, by the receiver, of the clock signal and the reference time. Storage unit 240 may include a memory for storing time specifics of (defining) a sensing time window that may be within the work cycle. Controller 260 may be configured, within the work cycle, to measure time elapsing from the reference time by using the clock signal, and, based on the elapsed time and time specifics, to operate SCA 112 to sense a localization signal during a time period overlapping with the sensing time window. Controller 260 may also be configured to transmit data representative of the sensed localization signal during the same work cycle or during a subsequent work cycle.

In-vivo imager 110 may also include a location and steering unit ("LSU") 272. LSU 272 may include sensing coil assembly (SCA) 112 for sensing localization signals generated, for example, by LSS 130 of FIG. 1. LSU 272 may also include a magnets steering unit ("MSU") 211 to facilitate maneuvering of in-vivo imager 110, for example through interaction with magnetic fields which are generated by a maneuvering system similar to magnetic maneuvering unit (MMU) 140 of FIG. 1. Data representing or derived from the EMF signals induced in SCA 112 may be transmitted, for example, to data recorder 120 by embedding the data in image frames and/or by using frames that may be dedicated to transfer of such data.

At the time of, or shortly after, imaging device 110 is swallowed or otherwise inserted, or after some predetermined delay (e.g., 2 minutes), imager 212 may start capturing images of areas of the GI system. Because natural light does not enter the intestinal tract, imager 212 does not require a light shutter, as opposed to 'regular' (i.e., non-swallowable) imagers. The function of the light shutter is, therefore, implemented by the darkness inside the intestinal tract and by intermittently illuminating the field of view ("FOV") of imager 212. Typically, the exposure time of imager 212 is 2-3 milliseconds. Imager 212 may include an image sensor that may be, or include, an array of photo sensor elements (e.g., pixels) such as 256×256, 320×320, 1 Mega pixel or any other suitable array. Imager 212 outputs image data 213 by using a pixel format corresponding to the used pixels. Each image data may represent a captured image and, optionally, additional selected portions thereof.

Frames generator 220 may receive image data 213 that represents a captured image, and produce a corresponding image frame (or "frame" for short) that contains image data 213. A frame typically includes a header field that contains information and/or metadata related to the frame itself (e.g., information identifying the frame, the serial number of the frame, the time the frame, the bit-wise length of the frame, etc.), and a payload field. The payload may include an uncompressed version of the image data and/or a compressed version thereof, and a decimated image. The payload may also include additional information, for example readout of sensing coils assembly (SCA) 210.

Controller 260 may controllably operate, among other things, illumination/light source 214 to illuminate areas traversed by in-vivo imager 110, and schedule the images capturing times accordingly. Controller 260 may use timing unit 114 to time the operation of illumination source 214 to illuminate, for example, four times per second to enable capturing four images per second, and the operation of transceiver 250 to concurrently transmit corresponding frames at the same rate or at a different rate. Controller 260 may use timing unit 114 to operate illumination source 214 to capture more images per second, for example seventeen images per second, and transceiver 250 to concurrently transmit corresponding frames at the same rate or at a different rate. Controller 260 may temporarily store captured images and related image frames in data storage unit 240. Controller 260 may also perform various calculations and store interim calculation results in data storage unit 240. Controller 260 may also use timing unit 114 to time the operation of sensing coils assembly (SCA) 112 (to implement the sensing window(s)), and to time the SCA 112 readout from which the position and/or orientation of in-vivo imager 110 may be deduced (e.g., by controller 260 or by an external system; e.g., data recorder 120). Controller 260 may also use timing unit 114 to time the writing (e.g., adding, appending, or otherwise embedding) of corresponding localization data (e.g., the sensing coils readout or a manipulated version thereof) into the corresponding frame; e.g., into a frame that is to be transmitted, for example, immediately after the output of the sensing coils is read. After frames generator 220 produces a frame for a currently captured image, and embedding localization data into the frame, controller 260 may use transceiver 250 to wirelessly transfer 242 the frame to data recorder 120. Data recorder 120 may be worn by the person whose GI system is to be imaged. Controller 260, by executing software or instructions, may carry out steps which are performed by any one of timing unit 114 and frame generator 220, and other functions in in-vivo device 110, and thus may function as these units.

In between transmission periods (e.g., within idle periods separating transmission periods), controller 260 may use timing unit 114 to operate illumination source 214 to capture an image during a predetermined time window within an idle period during which transceiver 250 is dormant, disabled, or inactive, the time window being referred to herein as an "imaging window". Controller 260 may also use timing unit 114 to operate SCA 112 and to read and process the output of SCA 112 during another predetermined time window within the idle period, the other time window being referred to herein as the "sensing window". Controller 260 may use timing unit 114 to time other activities of in-vivo imager 110 (e.g., receiving commands from data recorder 120, processing and executing the commands, etc.). Transceiver 250, controller 260, timing unit 114, frame generator 220, and a controlling part of light source 214 may be embedded within one microchip.

Data recorder 120 may also include a receiver or transceiver 244, a frame parser 270, and a processor 290 for managing them. Data recorder 120 may include additional components (e.g., USB interface, Secure Digital ("SD") card driver/interface, controllers, etc.), elements or units for communicating with (e.g., transferring data frames, data, etc. to) a processing and/or displaying systems that may be configured to process images and localization data originating from in-vivo imager 110, and related data.

Transceiver 244 may receive a data frame corresponding to a particular captured image, and frame parser 270 may parse the data frame to extract the various data contained therein (e.g., image data, decimated image associated with the particular captured image, localization data, etc.). In some embodiments, some data frames, which are referred to herein as "localization frames", may be dedicated to contain and transfer only or mostly localization data. Localization frames may, for example, include localization data but not image data. Using localization frames in addition to image frames that include localization data may enable reading the localization data (e.g., the output of the sensing coils assembly 210) at a rate that is higher than the images capturing rate. For example, n (n=1, 2, 3, . . . ,) localization frames may be interposed (e.g., 'inserted' between, in time sequence), for example, between image frames, to form therewith a stream of frames. TRU 122, SSU 124, and LDU 126 are described above in connection with FIG. 1. Processor 290, by executing software or instructions, may carry out steps which are performed by any one of TRU 122, SSU 124, and LDU 126, and other functions in data recorder 120, and thus may function as these units.

User workstation 230 may include a display or be functionally connected to one or more external displays, for example to display 202. Workstation 230 may receive frames (e.g., image frames, localization frames, etc.) or images from data recorder 120 and present them in real-time, for example as live video, or produce a video stream that also contains location and orientation information that may also be displayed on, for example, display 202. Workstation 230 may include a memory (e.g., memory 204) for storing the frames transferred from data recorder 120 and possibly related metadata, and a processor (e.g., processor 205) for processing the stored frames and related data. Workstation 230 may display selected images or a video clip (e.g., a moving image stream) compiled from such images, e.g., to a human operator, health care person, physician, etc.

FIG. 3A shows a sensing window 326 according to example embodiment. An in-vivo device may produce work cycles similar to work cycle 304. Work cycle 304 may include a transmission period 306 during which the in-vivo device may transmit a data frame, for example, an image frame. Work cycle 304 may also include an idle period 308 during which the in-vivo device may refrain from transmitting data. The in-vivo device may sense localization signals during transmission period 306 (sensing window 326 is shown partly overlapping transmission period 306). The in-vivo device may simultaneously transmit a data frame during transmission period 306 and sense localization signals during sensing window 326.

Each work cycle may have associated with it a reference time from or relative to which time specifics of a sensing window may be measured. The time specifics Tw1 and Tw2 (the onset and termination times, respectively) of sensing window 326 may be measured relative to a reference time that resides, occurs, or is within the time period defined by in an idle period, for example relative to reference time 322 (as shown at 312 and 314, respectively), or relative to a reference time that resides in or is within the time period defined by a transmission period, for example relative to reference time 324 (as shown at 316 and 318, respectively). Sensing windows in other transmission periods may be scheduled (e.g., their time specifics may be measured relative to the pertinent reference time) in the same manner as sensing window 326. For example, the time specifics defining sensing window 328 in transmission period 309 may be measured relative to reference time 307.

FIG. 3B shows a sensing window 342 according to another example embodiment. An in-vivo device may produce or define work cycles similar to work cycle 304. Work cycle 304 may include a transmission period 306 during which the in-vivo device may transmit data, for example, within a data frame. Work cycle 304 may also include an idle period 308 during which the in-vivo device may refrain from transmitting data.

Sensing window 342 is shown partly overlapping idle period 308. The time specifics Tw3 and Tw4 (the onset and termination times, respectively) of sensing window 342 may be measured relative to a reference time that resides in, or is within the time period defined by a transmission period, for example relative to reference time 352 (as shown at 334 and 336, respectively), or relative to a reference time that resides in or is within the time period defined by an idle period, for example relative to reference time 354 (as shown at 338 and 346, respectively). Sensing windows in other idle periods may be scheduled in the same manner as sensing window 342. Each work cycle may have associated with it a reference time from or relative to which time specifics of the respective sensing window may be measured.

FIG. 3C shows a block diagram of a timing unit 300 of an in-vivo device according to an example embodiment. Timing unit 300 may perform or enable performing tasks, activities, operations or processes, as described herein, and some or every activity and/or process performed by or attributed to timing unit 114 may also be performed by or attributed to timing unit 300, and vice versa. Timing unit 300 may include a master clock generator ("MCG") 310, a clock counter 320, a reset signal generator ("RSG") 330, a count comparator 340, a memory 350, and a sensing window signal ("SWS") generator 360. By "master clock generator" is meant a pulse generator that generates a clock signal that may be commonly used by the various circuits and components of the in-vivo device to synchronize their activities, tasks, etc. MCG 310 may be an integral part of timing unit 300 or external to timing unit 300. Master clock generator (MCG) 310, which may be, include, or use a free-running oscillator, may generate a clock signal 311 at a constant frequency $f_{OSC}$, for example at 8.1 megahertz (MHz). Clock counter 320 may continually count the clock pulses generated by MCG 310 to facilitate measurement or calculation of an elapsed time.

FIG. 3C will be described further in association with FIG. 3D, which shows a time diagram related to timing unit 300. The controller of the in-vivo device (e.g., controller 260 of in-vivo device 110) may use MCG 310 to time or schedule the various tasks that are executed by the in-vivo device. For example, the in-vivo device's controller, alone or in conjunction with another component/unit of the in-vivo device, may use MCG 310 to generate a frame signal F(t) (signal F(t) is shown at 302 in FIG. 3C and it is also shown in FIGS. 3A, 3B, and 3D), and use the frame signal F(t) to schedule the transmission of a data frame to occur between time t1 and time t2 (i.e., during transmission period 371, which is the transmission period of work cycle 370), between time t3 and time t4 (i.e., during transmission period 373, which is the transmission period of a work cycle following work cycle 370), etc.

Reset signal generator (RSG) 330 may use the transmission periods 371, 373, and so on, and the idle periods 372, etc. of frame signal F(t) to produce a reset signal R(t) (signal R(t) is shown at 332) that may include a series of reset pulses (e.g., reset pulses 381, 382, 383, and 384). RSG 330 may use reset signal R(t), or portion thereof (e.g., only R(t) pulses that represent off-to-on transitions in F(t)) to reset clock counter 320, for example, every time a transmission is (re)commenced (e.g., at times t1 and t3), and/or terminated (e.g., at times t2 and t4). That is, reset signal R(t) may include only one type of reset pulses; e.g., pulses representing only 'transmission-to-idle' (i.e., on-to-off) transitions (e.g., pulses 382, 384, etc.) or pulses representing only 'idle-to-transmission' (i.e., off-to-on) transitions (e.g., pulses 381, 383, etc.). Alternatively, reset signal R(t) may include both types of reset pulses (e.g., pulses, . . . , 381, 382, 383, 384, . . . ).

Clock counter 320 may be reset or initialized during each work cycle or during selected work cycles. Each time RSG 330 resets clock counter 320, which counts pulses of clock signal 311, the value of clock counter 320 may be reset, or initialized, to an initial value at a time overlapping with or coinciding with the reference time. (The initial value of clock counter 320 may be, for example, zero, or any value that is greater than zero.) The pulses counting range of clock counter 320 may be utilized internally, for example by the in-vivo device's controller, to measure, for example, a time elapsing from a reset pulse of a specific type, for example, from a reset pulse representing transition from a transmission period to an idle period. Each reset pulse, or selected reset pulses, in reset signal R(t) may indicate a reference time relative to which time specifics of sensing windows may be measured.

Memory 350 may hold time specifics of a sensing window, such as a first count value, N_1, that may be equivalent to or represent the onset time of the sensing window relative to a reset pulse, and a second count value, N_2 (N_2>N_1) that may be equivalent to or represent the termination time of the sensing window relative to the same reset pulse. For example, if, per timing constraints within idle period 372, a sensing window is to 'open' or start at time Tw5 and 'close' or terminate at time Tw6, the count values N_1 and N_2 may be chosen such that they respectively represent times 392 and 394 that elapse from, or relative to, a designated reset pulse, for example from, or relative to, reset pulse 382. The same count values N_1 and N_2 may likewise be reused for other work cycles.

Count comparator 340 may output a time indication each time the value of clock counter 320 reaches any of the count values N_1 and N_2, and sensing window signal (SWS) generator 360 may use the time indications that are output by count comparator 340 to produce a corresponding sensing window signal W(t) (signal W(t) is shown at 362). During the sensing window 364, the controller of the in-vivo device (e.g., controller 260 of in-vivo device 110) may transition to the sensing mode during which it may enable or activate sensing coils assembly (SCA) 112, read the output of SCA 112, process the output of SCA 112 and temporarily store corresponding localization data in a memory (e.g., in storage unit 240). The controller of the in-vivo device may embed the localization data obtained during a particular work cycle, for example, in the next data frame that is scheduled to be transmitted. For example, the controller of the in-vivo device may embed localization data that is obtained during idle period 372 in a data frame that is scheduled to be transmitted during transmission period 373, or in a data frame that is scheduled to be transmitted during a transmission period of some other work cycle. The embodiment shown in FIG. 3B (i.e., sensing windows that reside in or is within the time period defined by idle periods) is further elaborated below, for example, in connection with FIG. 6, FIG. 7, FIG. 8, and FIGS. 11A-11B, and similar principles, which are described in connection or in association with these figures, may likewise be applicable to the embodiment shown in FIG. 3A.

FIG. 4 shows a block diagram of a timing restoration unit ("TRU") 400 according to an example embodiment. Timing restoration unit (TRU) 400 may include a master clock and a reset signal restoration ("MCRR") unit 410, a pulse counter 440, a count comparator 450, a memory 460, and a sensing window signal (SWS) generator 470. MCRR unit 410 may include a clock restoration module ("CRM") 420 and an end-of-transmission ("EOT") detector 430. A data recorder (e.g., data recorder 120) may receive a data frame 402 from an in-vivo device, and data frame 402 may include suffix data bits.

As explained in connection with timing restoration unit (TRU) 122, suffix data of a data frame may be used to indicate the end-of-transmission (EOT) time of the data frame. In addition, the suffix data may contain data bits whose combination (e.g., . . . , 1, 0, 1, 0, 1, 0, . . . ,) enables restoration of the genuine clock pulses originally produced in and used by the in-vivo device with which the data recorder operates. CRM 420 may use data bits of the suffix data, or any other data bits, to restore the in-vivo device's master clock signal generated by a master clock generator identical or similar to, for example, master clock generator (MCG) 310 of FIG. 3C. CRM 420 may include a phased lock loop ("PLL"). The PLL may output a clock signal whose frequency may be determined based on, or tuned using, the data bits. Tuning the PLL may be performed continually (e.g., by using data bits in each data frame) or once in a while (e.g., once in k data frames, where k=1, 2, 3, 4, . . . ). EOT detector 430 may use suffix data bits to identify EOT times, and to produce a reset signal R'(t) 332' that corresponds to the EOT times. Reset signal R'(t) 332' may be a restored version of reset signal R(t) 332 of FIGS. 3C and 3D since the EOT times detected by EOT detector 430 correspond to the EOT times at the in-vivo device. By way of example, reset pulse 382' of FIG. 4 is a restored version of reset pulse 382 of FIG. 3D.

Pulse counter 440, count comparator 450, and sensing window signal (SWS) generator 470 may respectively function like clock counter 320, count comparator 340, and SWS generator 360 of FIG. 3C. The values N_3 and N_4, which may be stored in memory 460 and used by count comparator 450, may respectively be identical to the values N_1 and N_2, which may be stored in memory 350 and used by count comparator 340 of FIG. 3C. By using the values N_3 and N_4 count comparator 450 may output a time indication each time the value of pulse counter 440 reaches one of the values N_3 and N_4, and sensing window signal (SWS) generator 470 may use the time indications output by count comparator 450 to produce a corresponding sensing window signal W'(t) (signal W'(t) is shown at 362'). Sensing window signal W'(t) is a restored, or recovered, version of sensing window signal W(t) (signal W(t) is shown in FIG. 3D and at 362 in FIG. 3C). For various reasons (e.g., latency, etc.), the restored sensing window signal W'(t) may lag behind sensing window signal W(t), as shown, for example, in FIG. 8, which is described below. However, the values of N_3 and N_4 may be set or adjusted (e.g., by calculation or empirically) such that they accommodate for the delay (e.g., minimize the delay to an acceptable, manageable, or ignorable value).

Figure 5:
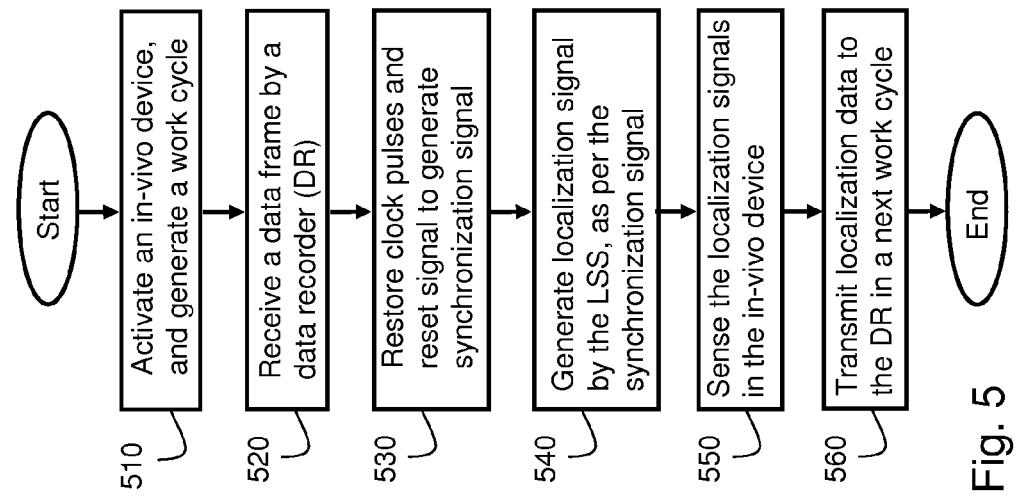
FIG. 5 shows a method for synchronizing between an in-vivo device and a localization signals source according to an example embodiment.

FIG. 5 shows a method for synchronizing between an in-vivo device and a localization signal generating system according to an example embodiment. At step 510, the in-vivo device (e.g., in-vivo device 110) may be activated and the in-vivo device may execute, generate or commence a work cycle similar, for example, to work cycle 370 of FIG. 3D. The work cycle may have a time period during which the in-vivo device may transmit a data frame. At step 520, a data recorder (e.g., data recorder 120) may receive the data frame transmitted from the in-vivo device. At step 530, the pulses of the master clock, which may originally be used by the in-vivo device to synchronize its operation, may be restored (e.g., by MCRR 410) in order to facilitate generation or creation of a synchronization signal by a synchronization signal unit similar to SSU 124 of FIG. 1.

At step 540, a localization signal may be generated by a localization signals source (LSS) similar to LSS 130 at a time and for a duration specified, indicated, or represented by the synchronization signal. As discussed above, the synchronization signal generated and output by, for example, SWS Generator 470 (e.g., W'(t)) and the sensing window signal W(t) used by the in-vivo device may be derived from a common time 'source' or time indicator (e.g., 'transmission-to-idle' transitions). Therefore, at step 550 the in-vivo device may activate sensing coils assembly (SCA) 112 to sense the localization signal substantially at the same time and substantially for the same period as specified, indicated, or represented by the synchronization signal. At step 560, the in-vivo device may pre-process the sensed localization signal (e.g., the EMF signal(s) induced, for example, in SCA 112), temporarily store corresponding localization data, and transmit the localization data (e.g., to the data recorder) during a transmission period of the next or subsequent work cycle, or during a transmission period of some other work cycle. Generation and transmission of work cycles may continue as long as possible or as long as required, as per step 510, and steps 520 to 560 may be repeated for each work cycle or for selected work cycles.

A method for synchronizing between an in-vivo device and a localization signal generating system according to another example embodiment may include defining a sensing window during which the in-vivo device may sense a localization signal; intermittently transmitting data from the in-vivo device; restoring, by a receiver (e.g., data recorder) external to the in-vivo device, the sensing window from data (e.g., a data frame) transmitted by the in-vivo device; producing, by the receiver, based on the restored sensing window, a synchronization signal to signal the sensing window; transferring the synchronization signal to a localization signals source (LSS); and generating by the localization signals source, and sensing by the in-vivo device, a localization signal during the sensing window. Any data that is transmitted as, or in the form of, data frames may be regarded as data that is transmitted intermittently. For example, image data may be regarded as data that is transmitted intermittently because it is transmitted using image frames.

Figure 6:
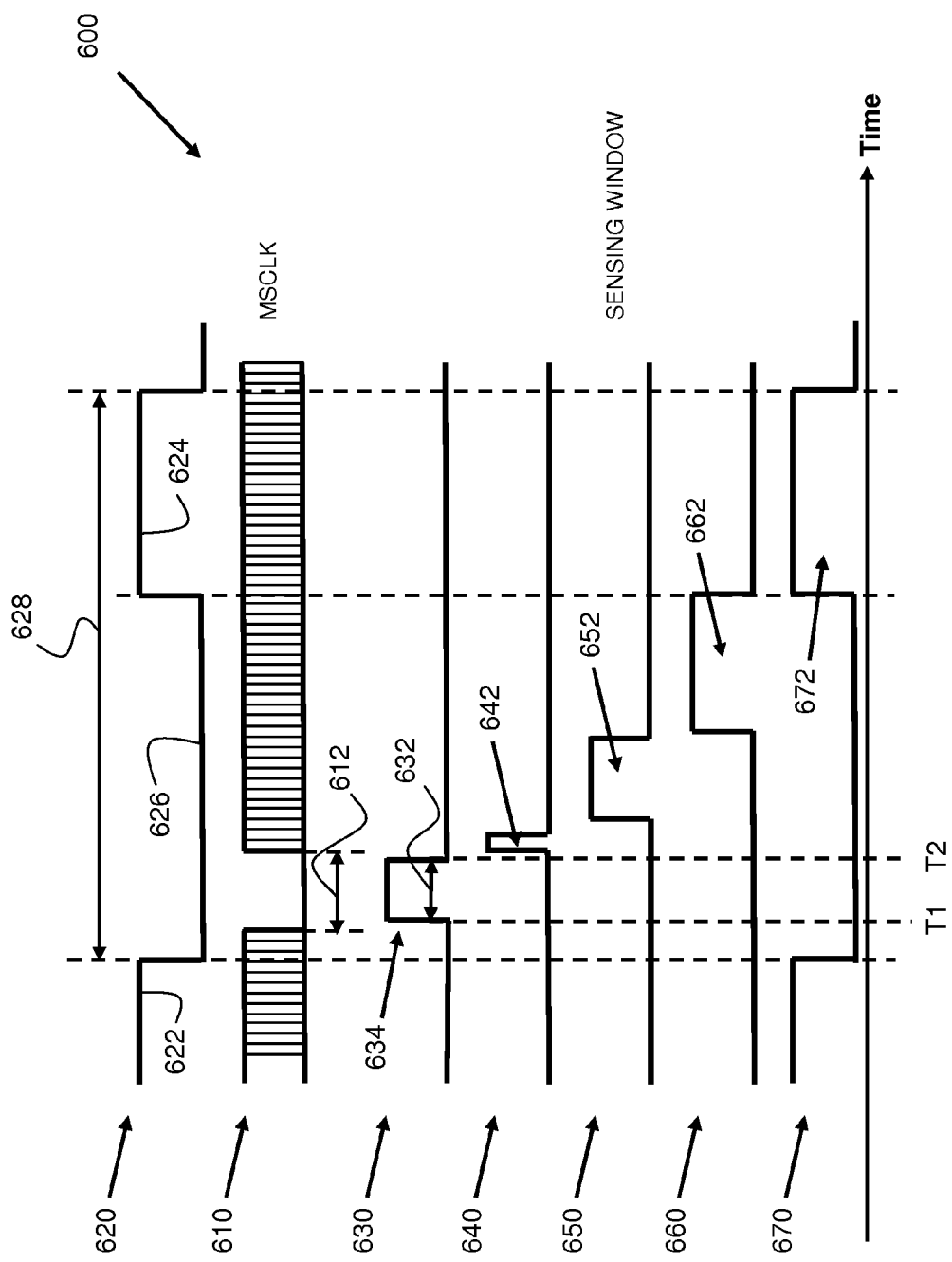
FIG. 6 shows various signals of an in-vivo device according to an example embodiment.

FIG. 6 shows a timing diagram 600 used internally by an in-vivo device according to an example embodiment. Graph 610 is a master clock (MSCLK) signal. MSCLK signal may be used internally by the in-vivo device to synchronize the activities performed by the in-vivo device. Graph 620 is a main signal that is timed based on MSCLK signal 610. That is, MSCLK signal 610 enables timing the logic value '1', or 'high' state, of main signal 620, as shown at 622 and 624, and the logic value '0', or 'low' state, of main signal 620, as shown at 626. MSCLK signal 610 may be generated by a timing unit similar to master clock generator (MCG) 310 of FIG. 3C.

The duration of the high states of main signal 620 (e.g., high states 622 and 624) may be set to comply with the transmission period discussed above (e.g., in connection with transmission periods 371 and 373 of FIG. 3D). The duration of the low states of main signal 620 (e.g., low state 626) may be set to comply with the idle periods discussed above (e.g., in connection with idle period 372 of FIG. 3D). Time cycle $T_{CYCLE}$ 628, which is an example work cycle, includes idle period 626 and transmission period 624.

Due to the relatively high frequency (e.g., in the order of megahertz) at which master clock generators typically operate, they tend to superimpose electrical noises on electrical signals, the result of which may be a degraded signal-to-noise (S/N) ratio. Disabling the output of the clock generator when it is not required, or limiting its use, for a limited time period within an idle period (e.g., within idle period 626), may, therefore, mitigate that problem. Disabling the output of the clock generator, or limiting its use, may mean that the clock generator may still produce clock pulses in order to keep track time, but these pulses are not used to 'clock' (they are not distributed to) other components. Temporarily disabling the output of the clock generator (or limiting its use) may, therefore, increase, or improve, the reception sensitivity of a receiver of the in-vivo device, and therefore may beneficially be used by the in-vivo device to receive commands and/or data from the data recorder. For example, during idle period 626 the output of the clock generator that generates MSCLK signal 610 may be disabled for a time period 612 to improve the reception quality of commands and/or data from the data recorder, and, in general, to reduce electrical noise in the in-vivo device.

Graph 630 is a signal ("DOWNLINK") that may signal to the in-vivo device's controller a time slot, or 'downlink' period, that has been allocated in each idle period, or in selected idle periods (e.g., downlink period 632 in selected idle period 626), during which the in-vivo device may receive commands and/or data from the data recorder. Graph 640 is a window signal that may signal to the in-vivo device's controller a time slot during which the in-vivo device may process commands and/or data that the in-vivo device may receive during, for example, downlink period 632 from the data recorder. The data recorder may occasionally transmit commands and/or data to the in-vivo device, and the in-vivo device may reserve downlink periods similar to downlink period 632 in order to be able to receive the commands and/or data, once transmitted by the data recorder. Graph 650 is a signal ("SENSING") similar to sensing window signal (SWS) 364 of FIG. 3D. Sensing signal 650 may signal to the in-vivo device's controller a time slot (e.g., a sensing window) during which the in-vivo device may prepare to receive localization signals (e.g., from localization signals source (LSS) 130), process the localization signals, and store corresponding localization data in a storage unit (e.g., in storage unit 240). Graph 660 is a window signal that may signal to the in-vivo device's controller a time slot (e.g., an imaging window) during which the in-vivo device may capture an image by, for example, activating, during window 662, the illumination source (e.g., light/illumination source 214) and the imager (e.g., imager 212), and executing related processes (e.g., image capturing and processing, storing image data, etc.). Graph 670 depicts a window signal similar to frame signal F(t) of FIG. 3B and FIG. 3D. Signal 670 may signal to the in-vivo device's controller a time slot (e.g., a transmission period) during which the in-vivo device may activate the transmitter (e.g., transmitter 250) and transmit a data frame (e.g., image frame). The data frame may include any combination of image data, localization data, prefix data bits, suffix data bits, and other types of data.

The time specifics of downlink pulse 634 (and of other like pulses); e.g., onset time T1 and termination time T2 of pulse 634, may be determined by using a timing unit similar to timing unit 300, with the count values N_1 and N_2 replaced by count values corresponding to or representing times T1 and T2 (which are measured or calculated relative to a predetermined reference time). Pulse/window 642 (and like pulses/windows), pulse/window 652 (and like pulses/windows), pulse/window 662 (and like pulses/windows), and pulse/window 672 (and like pulses/windows) may be timed like pulse/window 634; that is, by using corresponding count values N_i, N_j.

Figure 7:
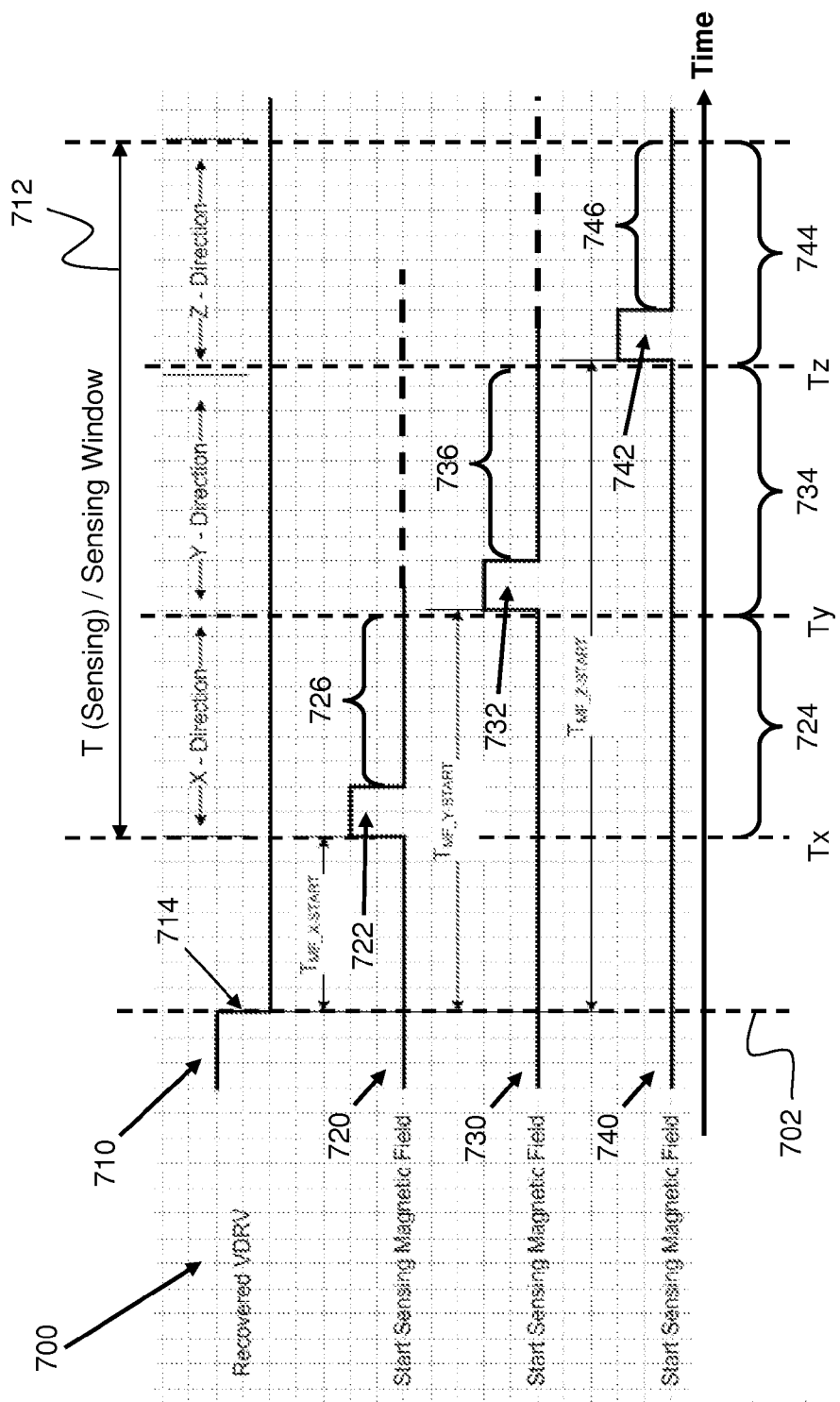
FIG. 7 shows sensing sub-windows according to an example embodiment.

FIG. 7 shows a timing diagram 700 that is used internally by a data recorder according to an example embodiment. Graph 710 is a recovered version of the main signal 620 in FIG. 6. Sensing window 712 is functionally similar to sensing window 342 of FIG. 3B, where the sensing window starts at time Tw3 and terminates at time Tw4, and to sensing window 652 of FIG. 6. Down-transition 714 (at time 702) may be used to reset a counter and trigger another count interval to determine the time boundaries of sensing window 712.

In one embodiment a location of an in-vivo device is determined by a localization system by using the X,Y,Z coordinates system, and the localization signals source (e.g., LSS 130) transmits three electromagnetic signals: one signal that is associated with or corresponds to the X-axis, and such signal is referred to herein as "X-signal"; a second signal that is associated with or corresponds to the Y-axis, and such signal is referred to herein as "Y-signal"; and a third signal that is associated with or corresponds to the Z-axis, and such signal is referred to herein as "Z-signal". The X-signal, the Y-signal, and the Z-signal may be transmitted one signal at a time, for example in order for them to be correctly interpreted by the in-vivo device. The overall time slot 712 allocated for sensing and processing localization signals may be partitioned to three sensing sub-windows 724, 734, and 744. Each sensing sub-window may be allocated to a particular localization signal. For example, sensing sub-window 724 may be allocated to sense the X-signal; sensing sub-window 734 may be allocated to sense the Y-signal; and sensing sub-window 744 may be allocated to sense the Z-signal. The X-signal, Y-signal, and Z-signal may be transmitted by a localization signal source (LSS) as per three, separate, synchronization signals 720, 730, and 740. The time specifics of synchronization signals 720, 730, and 740 may be measured from or relative to, for example, reference time 702. One synchronization signal may be used instead of the separate synchronization signals 720, 730, 740, and such a synchronization signal may embody (a superposition of) the separate synchronization signals.

In general, description in this document regarding the sensing window may in some embodiments apply to each sensing sub-window. The term "sensing sub-window" is merely used herein as a matter of convenience. Time specifics of a sensing sub-window may be measured by counting the same clock pulses that are used for measuring the time specifics of the 'larger' sensing window, and relative to the same time reference that is used for measuring the time specifics of the sensing window. 'Time specifics' may be explicitly expressed, measured or counted in time units (e.g., in seconds; e.g., 2 milliseconds), or implicitly, as a number of clock pulses or pulse count (e.g., 580 pulses). Measuring time that elapses relative to a reference time is equivalent to counting clock pulses relative to a reference, or initial, count value of a counter. Stating that sensing electromagnetic localization signal is done during a sensing window (or during a sensing sub-window) is analogous to stating that sensing the electromagnetic localization signal is done during a time period coinciding with the sensing window (or with the sensing sub-window).

The in-vivo device may start sensing the X-signal at time Tx and for the duration of pulse 722, and use the remaining time 726 of sub-window 724 to process the sensed X-signal and to store corresponding localization data in a storage unit. Likewise, the in-vivo device may start sensing the Y-signal at time Ty and for the duration of pulse 732, and use the remaining time 736 of sub-window 734 to process the sensed Y-signal and to store corresponding localization data in a storage unit. Likewise, the in-vivo device may start sensing the Z-signal at time Tz and for the duration of pulse 742, and use the remaining time 746 of sub-window 744 to process the sensed Z-signal and to store corresponding localization data in a storage unit. The up-transitions of pulses 722, 732, and 742 (which are respectively shown at, or respectively correspond to times Tx, Ty, and Tz) and the down-transitions (or duration) of each sensing sub-window may be determined by, for example, comparing corresponding pulse count values to time specifics that define the sensing sub-windows.

Figure 8:
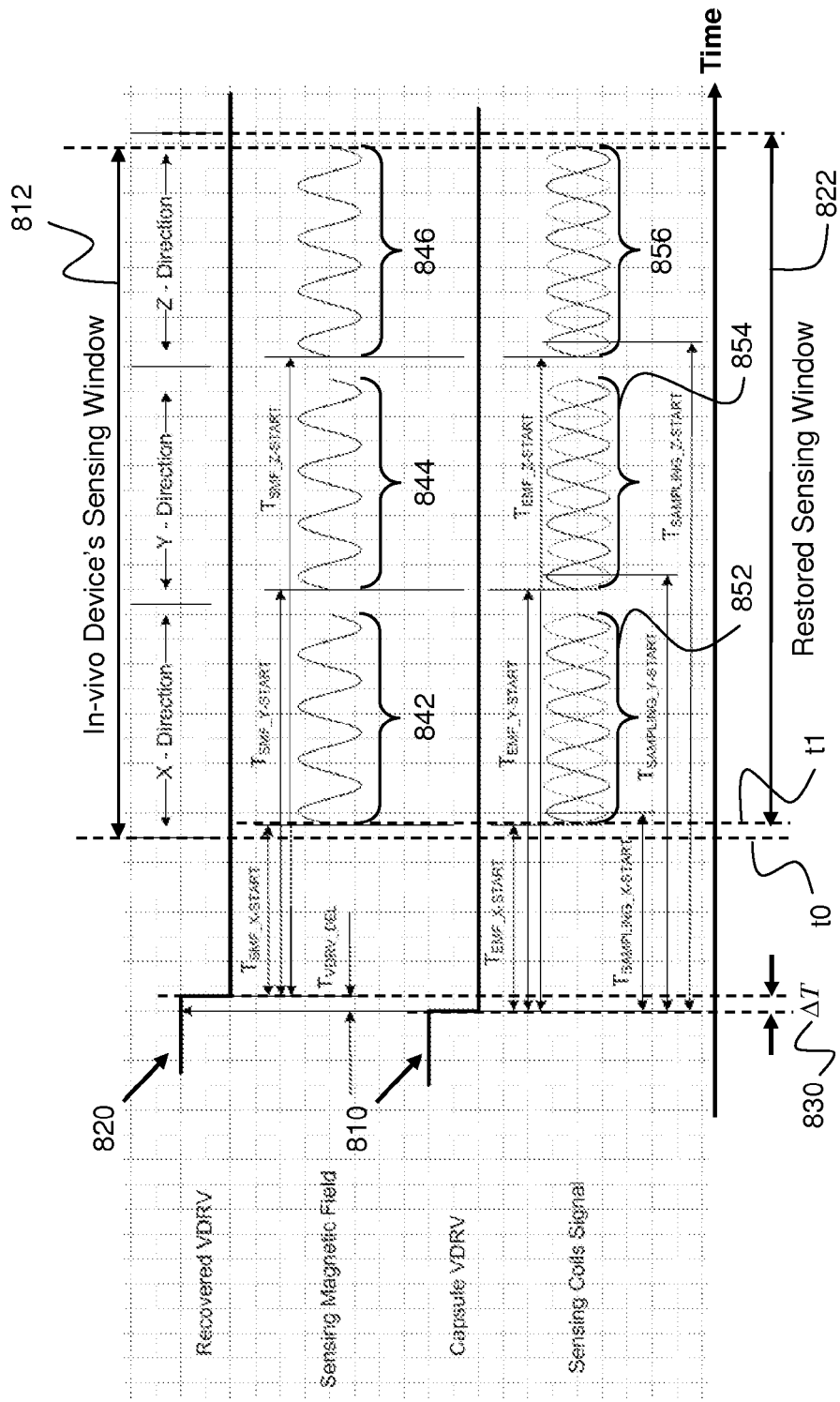
FIG. 8 shows localization signals and resulting sensed (EMF) signals timed according to an example embodiment.

FIG. 8 shows localization signals and resulting sensed signals (EMF signals) that are timed according to an example embodiment. Signal 810 is an example main signal that is generated in an in-vivo device (e.g., in in-vivo device 110). With main signal 810 is associated a sensing window 812, during which electromagnetic localization signals may be generated and transmitted (e.g., by LSS 130) and concurrently sensed by one or more sensing coils of the in-vivo device (e.g., by SCA 112).

Signal 820 (a recovered main signal) is a signal restored, for example, by a data recorder (e.g., data recorder 120), for example by using data bit, or data bits, (e.g., suffix data or any other group of data bits) embedded in data frames. The data bit(s) used for the signal restoration may be chosen such that the restored signal temporally resembles main signal 810 as much as possible in terms of shape and timing. A sensing window (e.g., sensing window 822) is also associated with main signal 820. Due to various factors (e.g., latency, etc.), main signal 820 (the restored main signal) may lag behind main signal 810 (main signal 810 is the in-vivo device's 'genuine' main signal). An example lag time $\Delta T$ between signal 810 and signal 820 is shown at 830. As a result of lag time 830, sensing window 822 may also lag behind sensing window 812. By way of example, sensing window 822 starts at time t1, whereas sensing window 812 starts at time t0, where $t1-t0=\Delta T$ (or $t1-t0 \cong \Delta T$). To continue the example, the in-vivo device may transition to the sensing mode at time t0 (to sense localization signals), and the system transmitting the localization signals based on main signal 820 may start transmitting the localization signals only at time t1. However, since $\Delta T$ is short (e.g., in the order of nanoseconds (nSec.), e.g., a few nSec.), it may have little or no impact on the electromagnetic signals sensing process and, therefore, on its results. The in-vivo device may reduce the lag time $\Delta T$ (i.e., fine tune to, or adjust or adapt sensing window 812 to sensing window 822; e.g., 'move' sensing window 812 to the right hand side (later in time) to coincide or overlap with sensing window 822) or compensate for it by manipulating (e.g., adjusting) the pertinent pulse count values. Data representative of the adjusted number(s) of pulses of the clock signal may be sent (transmitted, or otherwise communicated) to the in-vivo device (e.g., from a data recorder), or to the data recorder (e.g., from the in-vivo device).

A localization signals source (e.g., LSS 130) may transmit localization signals in short bursts. For example it may transmit, during a particular work cycle, a signal burst pertaining to the X-axis, then a signal burst pertaining to the Y-axis, then a signal burst pertaining to the Z-axis, and then it may repeat the sequence of signal bursts for each work cycle, or for selected work cycles. By way of example, electromagnetic localization signal burst 842 may be associated with the X-axis, and it may be transmitted first (starting at time t1), for example for a period set or governed by a pulse similar to pulse 722 of FIG. 7; electromagnetic localization signal burst 844 may be associated with the Y-axis, and it may be transmitted second, for example starting at a time and for a period set or governed by a pulse similar to pulse 732 of FIG. 7; and electromagnetic localization signal burst 846 may be associated with the Z-axis, and it may be transmitted third, for example starting at a time and for a period set or governed by a pulse similar to pulse 742 of FIG. 7. By way of example, each of localization signal bursts 842, 844, and 846 may include four cycles, as shown in FIG. 8, or other numbers of cycles (e.g., less than four cycles, or more than four cycles).

At time t0 or a short time after time t0 (e.g., at t1), the in-vivo device may start sensing electromagnetic localization signal burst 842: the resulting electromotive force (EMF) signal induced in a sensing coil of the in-vivo device by localization signal burst 842 is shown at 852. Shortly after localization signal burst 842 is terminated, the in-vivo device may process the sensed localization signal and thereafter may start sensing the next burst (electromagnetic localization signal burst 844): the resulting EMF signal induced in a sensing coil of the in-vivo device by localization signal burst 844 is shown at 854. Likewise, shortly after localization signal 844 is terminated, the in-vivo device may process the sensed localization signal and thereafter may start sensing electromagnetic localization signal 846: the resulting EMF signal induced in a sensing coil of the in-vivo device by localization signal burst 846 is shown at 856. Since an in-vivo device may be rotated, tilted, and rolled 360 degrees, an induced EMF signal may have a certain phase for a particular direction, alignment, or orientation of the related sensing coil, and an opposite phase for the opposite direction, alignment, or orientation of the sensing coil. For this reason, FIG. 8 shows two potential induced EMF signals for each of localization signal bursts 842, 844, and 846.

Figure 9:
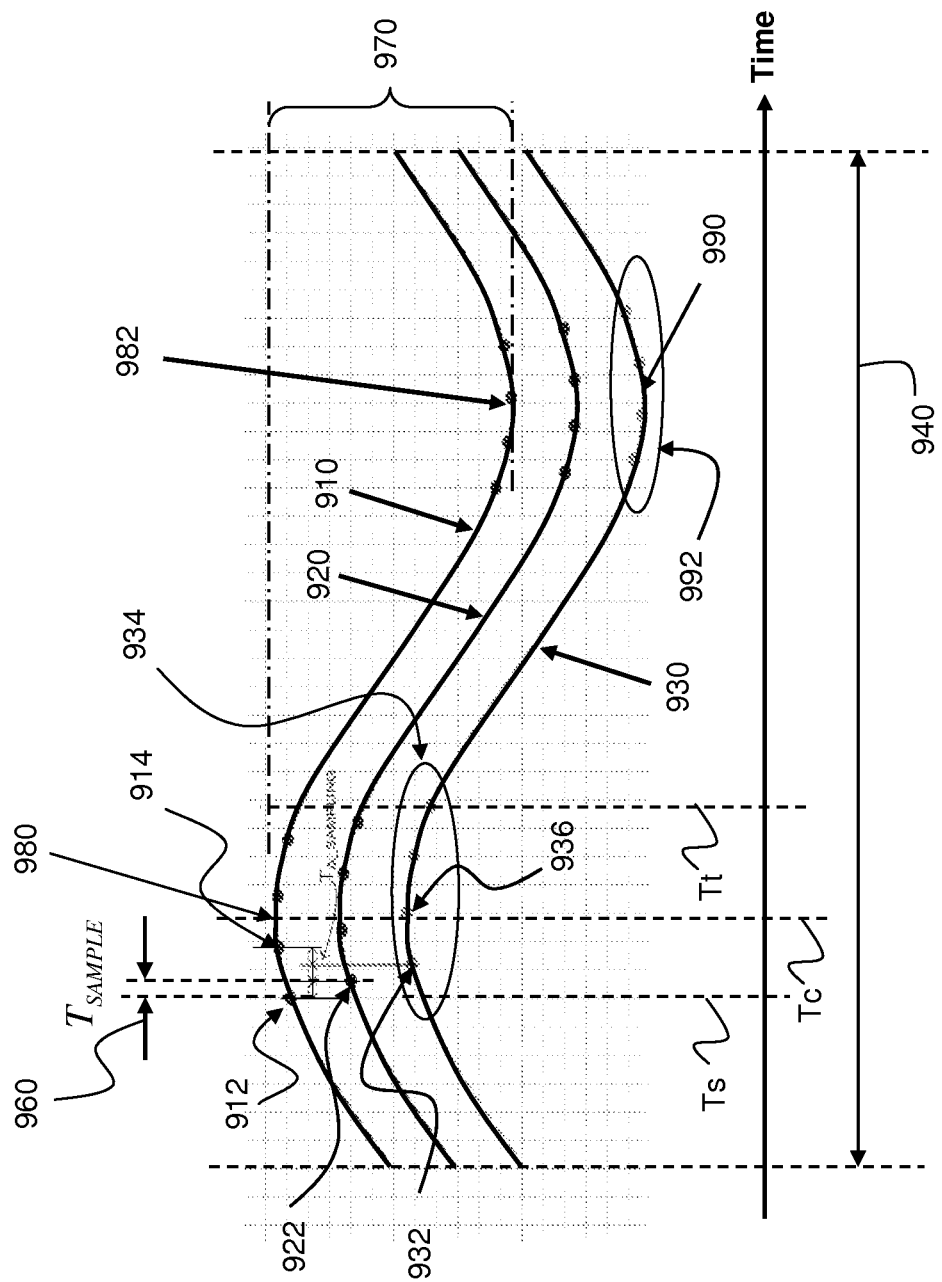
FIG. 9 shows example three EMF signals that are simultaneously induced on a sensing coils assembly (SCA) according to an example embodiment.

Practically, only one EMF signal can be induced in a sensing coil of the sensing coils assembly (SCA) of the in-vivo device at a time. If the sensing coils assembly (SCA) used by an in-vivo device includes n (n>1) sensing coils, each localization signal may induce an EMF signal in one or more of the n sensing coils. For example, if there are three localization signals (e.g., localization signals 842, 844, and 846) and n=3 (the SCA includes three, preferably mutually perpendicular, sensing coils), then up to nine EMF signals may be induced in the SCA altogether during sensing window 812: three EMF signals may simultaneously be induced in the three sensing coils by localization signal 842 during a first sensing sub-window; three EMF signals may simultaneously be induced in the three sensing coils by localization signal 844 during a second sensing sub-window, and three EMF signals may simultaneously be induced in the three sensing coils by localization signal 846 during a third sensing sub-window. For example, nine raw EMF signals such as raw EMF signals 852, 854, and 856 may be induced in the sensing coils of the SCA of the in-vivo device during each sensing window: EMFx1, EMFx2 and EMFx3 for the X-axis; EMFy1, EMFy2 and EMFy3 for the Y-axis; and EMFz1, EMFz2 and EMFz3 for the Z-axis. By "EMFxi", "EMFyi" and "EMFzi" (i=1, 2, 3) is respectively meant the EMF signals induced in the SCA's sensing coils by the localization signals respectively associated with the X-axis, Y-axis, and Z-axis. Example EMF signals that are induced in three sensing coils during a same sensing sub-window are shown in FIG. 9, which is described below. (The localization signals used to generate localization data do not necessarily have to be sinusoidal, as shown, for example, at 842, 844 and 846; they may have other shapes. For example, signal cycles making up a localization signal may substantially be triangularly shaped.)

Each burst of localization signal may include M cycles, where M may be equal to or greater than one. By way of example, each of localization signal bursts 842, 844, and 846 includes four cycles, in which example M=4. Each signal burst may induce, for example, three raw EMF signals (e.g., in SCA 112). At least one cycle has to be read from the sensing coils for each coordinate, direction, or orientation of the in-vivo device in order to be able to correctly deduce the coordinate, direction or orientation of the in-vivo device. However, reading one cycle for each coordinate/direction/orientation may not suffice. In general, the larger M, the higher the reliability of the reading of the induced EMF signals, and therefore the more accurate their interpretation. However, as discussed herein, the sensing window may be subjected to strict timing constraints, and using an EMF localization signal that includes too many cycles may result in one or more cycles exceeding the permitted boundaries of the sensing window or the permitted boundaries of the sensing sub-windows. That is, a sensing window, or sensing sub-window, can accommodate a maximal number, Mmax, of cycles. The aforesaid problem may be mitigated (e.g., Mmax may be increased) by shortening the cycles of the localization signals by increasing their frequency, $f_{LOC}$. Therefore, there is a tradeoff between the frequency of the localization signals ($f_{LOC}$), the maximal number (Mmax) of cycles that each localization signal burst is allowed to include, and the number of the used localization signals (e.g., three localization signals that may be related to the X,Y,Z coordinates system). The number of cycles (M) included in localization signal bursts may also depend on, and adjustable according to, the image capturing rate, or FPS value. In general, the higher the image capturing rate, the shorter the time that can be allocated for the sensing window and, therefore, the lesser the permitted number of the cycles of each signal burst. For example, if a sensing window's width (duration) is, for example, 5 milliseconds and the localization signals' frequency is, for example, 5 kilohertz (KHz), then the sensing window may theoretically be able to accommodate 25 cycles (M=25). Since processing of each EMF signal may take place in between bursts of localization signals, the practical usable number of cycles may be lower. For example the practical usable number of cycles may be 12, as shown in FIG. 8, where each of the three example localization signal bursts includes four cycles.

FIG. 9 shows an example of three EMF signals 910, 920, and 930 that are simultaneously induced (e.g., by a same localization signal burst) on a sensing coils assembly (SCA) that includes three sensing coils. For the sake of demonstration, EMF signals 910, 920, and 930 are graphically shown one under the other and having the same peak-to-peak amplitude 970. However, in a case where sensing coils have different spatial orientation (e.g., they may be mutually perpendicular), each sensing coil may, in general, output an EMF signal with a different peak-to-peak amplitude even if the sensing coils are subjected or exposed to the same localization signal.

As explained above, one localization signal may be generated outside the in-vivo device and sensed by the sensing coils assembly (SCA) of the in-vivo device for the X-axis, another localization signal may likewise be generated and sensed for the Y-axis, and another localization signal may likewise be generated and sensed for the Z-axis. That is, detecting the X,Y,Z coordinates of an in-vivo device may require generation of three localization signals by localization signals source (LSS) 130: one for the X-coordinate, another for the Y-coordinate, and another for the Z-coordinate. Depending on the orientation of the sensing coils of SCA 112 relative to LSS 130, whenever a particular localization signal is generated, it may induce one, two or three EMF signals: one EMF signal on the sensing coil associated with the X-axis, another EMF signal on the sensing coil associated with the Y-axis, and another EMF signal on the sensing coil associated with the Z-axis. By way of example, EMF signals 910, 920, and 930 are assumed to be induced on three sensing coils by a same localization signal. For example, EMF signals 910, 920, and 930 (or similar EMF signals) may be induced by the localization signal associated with the X-axis, in which case the X-coordinate of the in-vivo device may be deduced from EMF signals 910, 920, and 930. If EMF signals 910, 920, and 930 (or similar EMF signals) are induced by the localization signal associated with the Y-axis, then the induced EMF signals enable determining the Y-coordinate of the in-vivo device, and if EMF signals 910, 920, and 930 (or similar EMF signals) are induced by the localization signal associated with the Z-axis, then the induced EMF signals enable determining the Z-coordinate of the in-vivo device. That is, a set of three (or other numbers of) EMF signals may serve as a basis for determining or deducing a particular coordinate (or orientation) of the in-vivo device. EMF signals 910, 920, and 930 (which make up an example set of EMF signals) may enable determination of one coordinate of the in-vivo device; another set of three (or other numbers of) EMF signals may serve as a basis for determining or deducing another coordinate (or orientation) of the in-vivo device, and so on.

The peak-to-peak amplitudes of EMF signals 910, 920 and 930, may be determined by a processor or controller (for example by controller 260 of in-vivo device 110), and the pertinent coordinate (be it the X-coordinate, the Y-coordinate, or the Z-coordinate) may be calculated or deduced (e.g., by the in-vivo device or externally) from these amplitudes, for example by using a suitable set of voltage-to-coordinate conversion formulas or tables. The in-vivo device may determine the peak-to-peak amplitudes of EMF signals 910, 920, and 930 by sampling at least a portion of each EMF signal and processing the samples. Then, the in-vivo device may store a corresponding sensing data for each sampled EMF signal in a storage device. The in-vivo device may sample each of EMF signals 910, 920, and 930, for example by allocating a separate sampling circuit, or sampler, for each sensing coil, or by using a common sampler. A sampler may include at least a sample-and-hold (S&H) circuit for analogically sampling EMP signals, and an analog-to-digital converter (ADC) for converting the analog sample values to digital data. A sampler may also include a preamplifier for amplifying the EMF signals before they are sampled by the S&H circuit.

In one embodiment EMF signals 910, 920, and 930 are sampled using a common sampler and the localization signals start from zero value and their first half is positive. Since the frequency, $f_{loc}$, and therefore the wavelength (e.g., wavelength, $\lambda$, 940), of the localization signals are known in advance, the positive peak, or crest, of the EMF signal may be expected (e.g., by using count comparator 340) to occur at time Tc. Therefore, the in-vivo device may schedule the sampling process to commence a short time before time Tc, for example at time Ts, and to terminate a short time after time Tc, for example at time Tt. Selecting a suitable sampling time (e.g., $T_{SAMPLE}$, shown at 960) may enable, for example, sampling the positive half of EMF signal 910 four times to find; e.g., by interpolation, a crest point; e.g., crest point 980, and sampling the negative half of EMF signal 910 four times to find, e.g., by interpolation, a lowest point in signal 910; e.g., point 982.

Likewise, sampling time $T_{SAMPLE}$ 960 may also enable, for example, sampling the positive halves of EMF signals 920 and 930 four times (to detect or deduce the respective crest points), and sampling the negative halves of EMF signals 920 and 930 four times (to detect or deduce the respective lowest points). Each group of 'positive' samples that are associated with the same EMF signal and each group of 'negative' samples that are associated with the same EMF signal may undergo an interpolation process to deduce or determine the pertinent crest point and lowest point, as the case may be. For example, positive samples group 934 enables determining the crest point 936, and negative samples group 992 enables determining the lowest point of EMF signal 930 (e.g., point 990).

A sampled point may be a crest point (e.g., crest point 936) or a lowest point, and if it is neither of those points, the crest point, or the lowest point, may be interpolated from the pertinent group of samples (e.g., crest point 980 and lowest point 990 may be interpolated from the pertinent samples group). Knowing the crest point and the lowest points of each EMF signal enables calculating its peak-to-peak amplitude (e.g., peak-to-peak amplitude 970). The order at which the EMF signals are sampled may be 'cyclic', with EMF signal 910 sampled first (e.g., at point 912), then EMF signal 920 sampled second (e.g., at point 922), then EMF signal 930 sampled third (e.g., at point 932), EMF signal 910 sampled again (e.g., at point 914), and so on.

Controller 260 of in-vivo device 110 may sample each cycle of each EMF signal, calculate, for example, an average peak-to-peak amplitude for each EMF signal (and nine average amplitudes in total for each work cycle or sensing window) and, while in the idle period (for example), store raw sensing data (raw localization data) corresponding to or representing the nine average peak-to-peak amplitudes. Controller 260 may embed the raw sensing/localization data in a data frame and transmit the data frame, for example, to data recorder 120, during one of the transmission periods following the idle period. Processor 290 of data recorder 120 may process the received raw sensing/localization data corresponding to or representing the nine average peak-to-peak amplitudes to deduce the X,Y,Z coordinates of the in-vivo device. Alternatively, data recorder 120 may transfer the raw sensing/localization data to another system for analysis.

Alternatively, controller 260 may process the EMF signals and deduce therefrom, for example, the X-Y-Z coordinates and/or the orientation of the in-vivo device. Controller 260 may, for example while the in-vivo device is in the idle period, store localization data that explicitly represent the X,Y,Z coordinates (and optionally the orientation) of the in-vivo device, and embed the data in a data frame. Controller 260 may transmit the data frame, for example, to data recorder 120, during a transmission period. Transmitting to the data recorder data that explicitly/already represent the X,Y,Z coordinates (and optionally the orientation) of the in-vivo device obviates the need for deducing these parameters by the data recorder or by another system.

Figure 10:
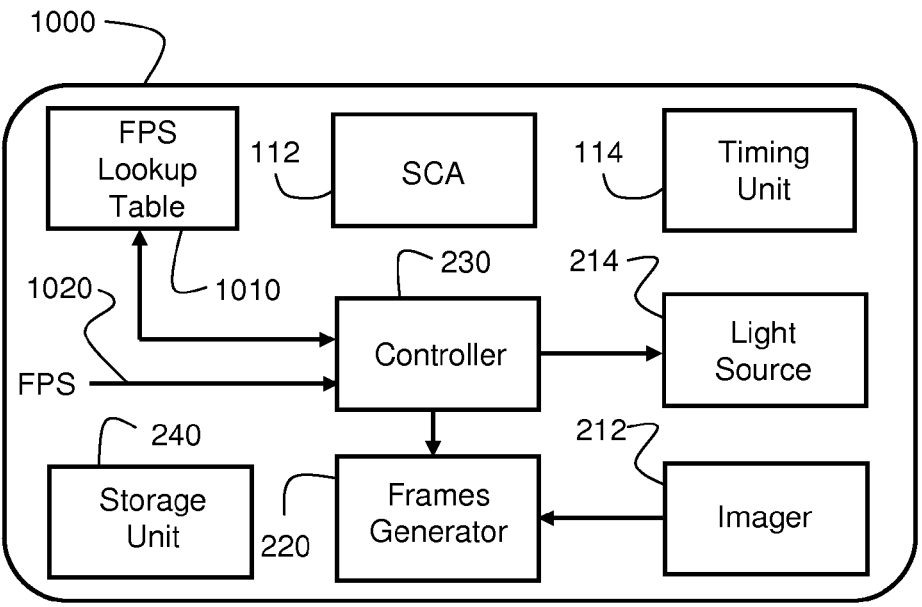
FIG. 10 shows an in-vivo device capable of adapting the time specifics of a sensing window according to a frames-per-second ("FPS") rate used by the in-vivo device according to an example embodiment.

FIG. 10 shows an in-vivo device 1000 that is configured according to another example embodiment. In-vivo device 1000 may include a FPS lookup table ("FLT") 1010 in addition, for example, to SCA 112, timing unit 114, imager 212, lighting source 214, frame generator 220, controller 260, storage unit 240, and other components that are shown in FIG. 2 (e.g., transceiver 250). FLT 1010 may facilitate adjustment of the sensing window and/or sensing sub-windows according to the used image capturing rate.

An in-vivo device may be capable of changing the image capturing rate or the rate at which the in-vivo device transfers images to the data recorder (that rate being referred to as, or measured in, frames per second (FPS)). The image capturing rate may change, for example, based on the location of the in-vivo device in the GI system and/or based on the imaged object and/or based on movement of the in-vivo device relative to the GI system, etc. A change in the image capturing rate may necessitate a change in the sensing window. That is, the time specifics of the sensing window may have to change (e.g., the window may have to be moved and its width or duration may have to be changed) to accommodate for changes in the image capturing rate or FPS. Controller 260 may receive a command 1020 (e.g., from the data recorder; e.g., during downlink window 634), for example, to change a current FPS value to another value. For example, controller 260 may receive a command 1020 to change the FPS rate from 4 FPS to 8 FPS, or from 2 FPS to 8 FPS, etc. Controller 260 may independently change the FPS rate, for example, based on a physical parameter (e.g., pH, temperature, pressure, movement, etc.) reaching a predetermined limit, or being within a specified range, or exceeding a specified range.

Referring to FIG. 6 again, if the FPS rate is increased, sensing window 652 may have to be moved to the left (on the time axis, e.g., prior in time) and it may have to be temporally narrower (shorter in duration) in order not to interfere with, for example, pulses/windows 642 and 662. Time specifics of sensing windows and/or time specifics of sensing sub-windows may be predetermined for different FPS values such that a particular sensing window, or a particular set of sensing window and related sensing sub-windows may be associated with a particular FPS value.

FLT 1010 may contain a list of FPS values and a list of pairs of count values (e.g., pairs [N_p11, N_p21]; [N_p12, N_p22]; [N_p13, N_23]; . . . , etc.), a pair per FPS, where each pair of count values may uniquely represent timing specifics of a different sensing window or sensing sub-window. "Different sensing window" and "different sensing sub-window" also refer to a sensing window and sensing sub-window that are temporally 'moved', adjusted, or adapted to accommodate for a new FPS rate, and to time specifics corresponding to, representing, or defining, the moved/adjusted/adapted sensing window or sensing sub-window. If three (or other numbers of) sensing sub-windows are additionally or alternatively used, FLT 1010 may include more than one pair of count values per FPS value (e.g., three pairs of count values, four pairs of count values, etc.). Each FPS value may, therefore, point to or be related to or associated with a set of pairs of count values. The set of pairs of count values may include pairs of count values related, for example, to a sensing window and/or to one or more sensing sub-windows. FLT 1010 may be stored, for example, in storage unit 240. If an in-vivo device receives a command (e.g., command 1020), for example from a data recorder, to use, or to transition to, a FPS rate that is not listed in PLT 1010, the in-vivo device (e.g., controller 260) may interpolate the time specifics or count values of the sensing window from the FPS values and from the pairs of count values that are listed in FLT 1010.

Figure 11A:
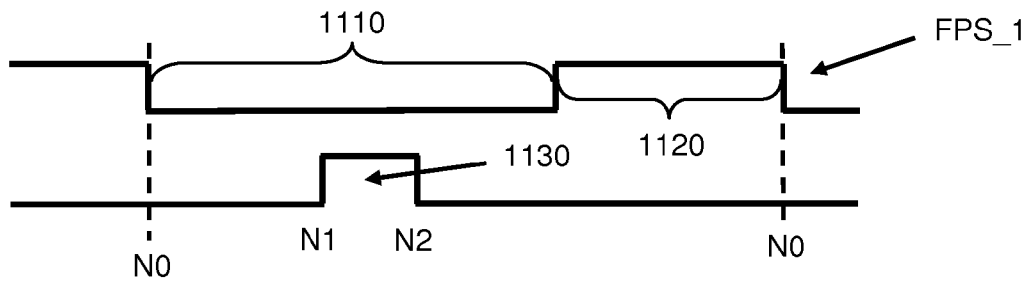
FIGS. 11A and 11B show timing diagrams associated with the sensing window adaptation of the in-vivo device of FIG. 10 according to an example embodiment.
Figure 11B:
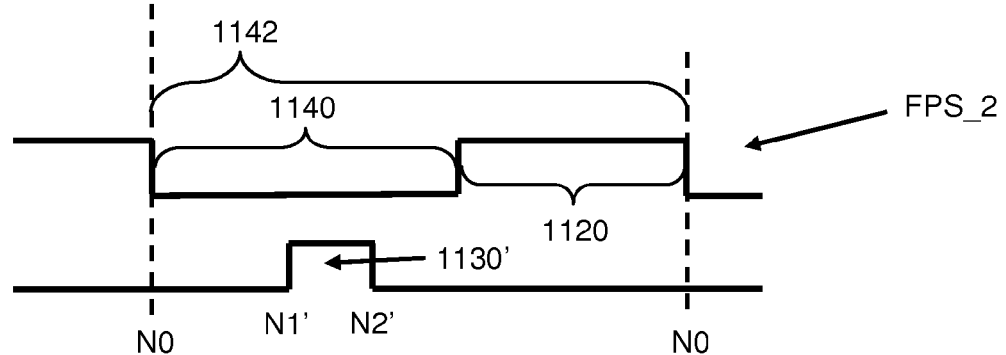

FIGS. 11A-11B show timing diagrams associated with the sensing window adaptation of the in-vivo device of FIG. 10. FIG. 11A shows a work cycle of an in-vivo device for a FPS value equal to FPS_1 (e.g., FPS_1=4 frames per second). The work cycle includes an idle period 1110 and a transmission period 1120. FIG. 11A also shows an example sensing window 1130 with an example pair of count values Ns1 and Ns2 that respectively represent particular starting time Ts and termination time Tt. As discussed in connection with FIG. 10, count values may be selected or determined per FPS value. In one embodiment count values Ns1 and Ns2 are selected or determined for a FPS value equal to FPS_1 (e.g., FPS_1=4 frame per second). Time specifics of sensing window 1130 may be constant or they may be adjusted or varied, for example, contingent on a rate (FPS) at which the in-vivo device transmits data (e.g., image data), as demonstrated in FIG. 11B, which is described below.

FIG. 11B shows a working cycle of the in-vivo device for a FPS value equal to FPS_2, where FPS_2>FPS_1 (e.g., FPS_2=8 frames per second). Accordingly, idle period 1140 is shorter than idle period 1110. (Since transmission periods do not necessarily depend on the FPS value (they may depend on other factors; e.g., compression of data, amount of data), the same transmission period 1120 is shown unchanged in FIG. 11B.) By way of example, FIG. 11B shows the sensing window 1130 of FIG. 11A adjusted in accordance with the adjusted work cycle (the adjusted work cycle is shown at 1142, by 'moving' it to the left, e.g., earlier in time (the moved sensing is shown at 1130'). Moving sensing window 1130 is implemented by respectively adjusting count values N1 and N2 to count values N1' and N2'. Count values N1' and N2' respectively represent adjusted starting time and adjusted termination time of adjusted sensing window 1130'. 'N0' in FIGS. 11A-11B is an initial count value. As explained above (for example in connection FIG. 3D), the initial value of the pulse counter may be '0', and the counter may be reset to the initial value, for example during each work cycle. The reset time may overlap or coincide with, or represent, the reference time relative to which time specifics are measured or calculated. Time specifics of sensing time sub-windows may be adjusted in the same manner as the time specifics of the sensing window, for example they may be adjusted proportionately to the adjusted time specifics of the sensing window, and, in that sense, the time specifics of the sensing time sub-windows are also adjusted or varied contingent on the data transmission rate, FPS, of the in-vivo device. Data representing the adjusted time specifics, or data representing the pertinent adjusted counted number(s) of pulses of the used clock signal, may be sent (e.g., transmitted, or otherwise communicated) to the in-vivo device (e.g., from a data recorder), or to the data recorder (e.g., from the in-vivo device).

As discussed, each burst of localization signal may include M cycles. In some embodiments, the frequency, $f_{LOC}$, of the localization signals may be constant, and the value of M may be inversely dependent on the image capturing rate: the higher the image capturing rate, the lower the value of M. The image capturing rate may controllably be adjustable between a minimum FPS limit FPSmin (e.g., FPSmin=2 FPS) and a maximum limit FPSmax (e.g., FPSmax=48 FPS), and M may be inversely adjusted between a minimum limit Mmin (e.g., Mmin=2 cycles) and a maximum limit Mmax (e.g., Mmax=6 cycles), where Mmin and Mmax are respectively associated with FPSmax and FPSmin. In other embodiments, the frequency, $f_{LOC}$, of the localization signals may be variable to enable maintaining the value of M: if the image capturing rate is increased, $f_{LOC}$ may be increased as well in order to maintain the value of M even though increasing the image capturing rate may result in narrowed sensing windows or narrowed sensing sub-windows.

As discussed, when the image capturing rate changes, time specifics of the sensing window, or sensing sub-windows, may have to be changed as well. A list of time specifics may be stored in, for example, the in-vivo device, and the in-vivo device may transfer the time specifics in force, for example, to the data recorder, or vice versa. In addition, if the frequency of the localization signals is adjustable and the image capturing rate changes from a current FPS to another FPS, the data recorder may send a message to the localization signals system (LSS), notifying it of a frequency of the localization signals that corresponds to the other FPS. In response to the message sent by the data recorder, the LSS may generate localization signals at the designated frequency. In another embodiment, the frequency of the localization signals may be constant, in which case the number of cycles of the localization signal, per each signal burst, may be adjustable in response to an adjustment of the sensing time window or sensing time sub-window. If the PFS rate changes, data that represents the new (adjusted) frequency of the localization signals or the new (adjusted) number of cycles of localization signal bursts (whichever the case may be) may be transmitted to the localization signals source.

FIG. 12A and FIG. 12B depict a printed circuit board ("PCB") of an in-vivo device that is configured to sense localization signals. FIG. 12A depicts an example cross-like multilayered imaging and sensing printed circuit board (MISP) 1200 of an in-vivo device similar to in-vivo imaging device 110. MISP 1200 may include 1-layer portions or sections even though it is generally referred to as a 'multi-layered' PCB. MISP 1200 may be rigid-flex, which means that portions, parts or sections thereof may be rigid whereas other portions, parts or sections thereof may be flexible enough to allow them to be folded into a cylinder-like structure. MISP 1200 may be full-flex, which means that all of its portions/parts/sections are flexible. By way of example, MISP 1200 is shown including two printed circuit board ("PCB") branches that 'cross', or intersect, each other: imager section 1240 and sensing coils assembly (SCA) section 1250.

Imager section 1240 includes at least imaging circuitry 1260, for which reason section 1240 is referred to as 'imager section'. Imager section 1240 may include, for example, three rigid sections, designated as 1202, 1204 and 1206, that may be multilayered, and two flexible sections, designated as 1294 and 1296, that may also be multilayered. Flexible section 1294 may connect rigid sections/portions 1204 and 1206 and be partly sandwiched between layers of these sections/portions. Section 1296 may connect rigid sections 1202 and 1204 and be partly sandwiched between layers of these sections. The other side of sections 1202, 1204, and 1206 may also accommodate additional elements and/or components, as depicted in FIG. 12B.

Imaging circuit 1260, which may include an imager similar to imager 212 of imaging device 110, may be mounted, for example, on rigid section 1206. An illumination source similar to illumination source 214 of in-vivo device 110 may also be mounted on rigid section 1206, as shown, for example, at 1270. By way of example, the illumination source mounted on rigid section 1206 includes four light sources which are equidistantly and circle-wise positioned on rigid section 1206. Other electronic components of the in-vivo device (e.g., ASIC, controller, transmitter, crystal oscillator, memory, etc.) may be mounted, for example, on section 1204 and/or on section 1202.

SCA section 1250 includes sensing coils for sensing (localization) magnetic fields by which the location and/or orientation of the in-vivo device may be determined By way of example, SCA section 1250 includes electromagnetic sensing coil 1210 and electromagnetic sensing coil 1220. Electromagnetic sensing coils 1210 and 1220 are shown to be rectangular, but they need not be rectangular. The two sensing coils 1210 are collectively referred to as sensing coil 1210 because the two sensing coils 1210 may be electrically interconnected to functionally form one electrical component (i.e., one sensing coil). Likewise, the two coils 1220 are collectively referred to as sensing coil 1220 because the two coils 1220 may be electrically interconnected to functionally form one sensing coil. An additional sensing coil, which may functionally be part of SCA section 1250, may be mounted on, or be embedded, incorporated into, built into or formed in rigid section 1202 (the additional sensing coil is shown at 1230). SCA section 1250 may be multilayered to accommodate sensing coils of enlarged inductance to increase the electromagnetic fields sensing sensitivity.

Flexible multilayered PCB dielectric substrate 1208 may accommodate sensing coils 1210 and 1220. Each PCB layer of multilayered PCB substrate 1208 may accommodate some of the coil turns of sensing coils 1210 and/or some of the coil turns of sensing coils 1220. SCA section 1250 is shown in FIGS. 12A and 12B outspread. Cylindrically folding SCA section 1250 places some turns of sensing coils 1210 against/opposite other turns of sensing coils 1210 (as shown in FIG. 12D) such that their normal lines substantially coincide with a same axis (e.g., 'X' axis of the X-Y-Z coordinates system), and some turns of sensing coils 1220 against/opposite other turns of sensing coils 1220 such that their normal lines substantially coincide with another same axis (e.g., 'Y' axis of the X-Y-Z coordinates system). (The opposing sensing coil 1220 is hidden in FIG. 12D, and the planes of sensing coils 1220, though curved a little, are generally perpendicular to the planes of sensing coils 1210.)

FIG. 12B shows the other side of MISP 1200. By way of example, section 1202 accommodates an antenna 1280 to facilitate radio frequency (RF) communication between the in-vivo imaging device and the data recorder or receiver with which the in-vivo imaging device operates; and sections 1204 and 1206 respectively accommodate electrical springs 1290 and 1292.

Imaging section 1240 is shown in FIGS. 12A and 12B outspread, but, to facilitate assembling of the in-vivo device, it is made foldable such that the rigid sections thereof may be stacked in a parallel manner such that rigid sections 1204 and 1206 may hold there between one or more batteries while the lines normal to the planes of sections 1204 and 1206 coincide with a longitudinal axis of the in-vivo imaging device. When rigid sections 1204 and 1206 are folded, electrical springs 1290 and 1292 secure the one or more batteries in place, and electrically connect them to the imaging device's electrical circuit (e.g., to MISP 1200). FIG. 12C shows a partly assembled in-vivo imaging device, with the imaging section 1240 folded/introverted and the SCA section 1250 cylindrically folded. FIG. 12D shows the partly assembled in-vivo device of FIG. 12C with an optical head 1262 mounted on top of rigid section 1206.

Figure 13A:
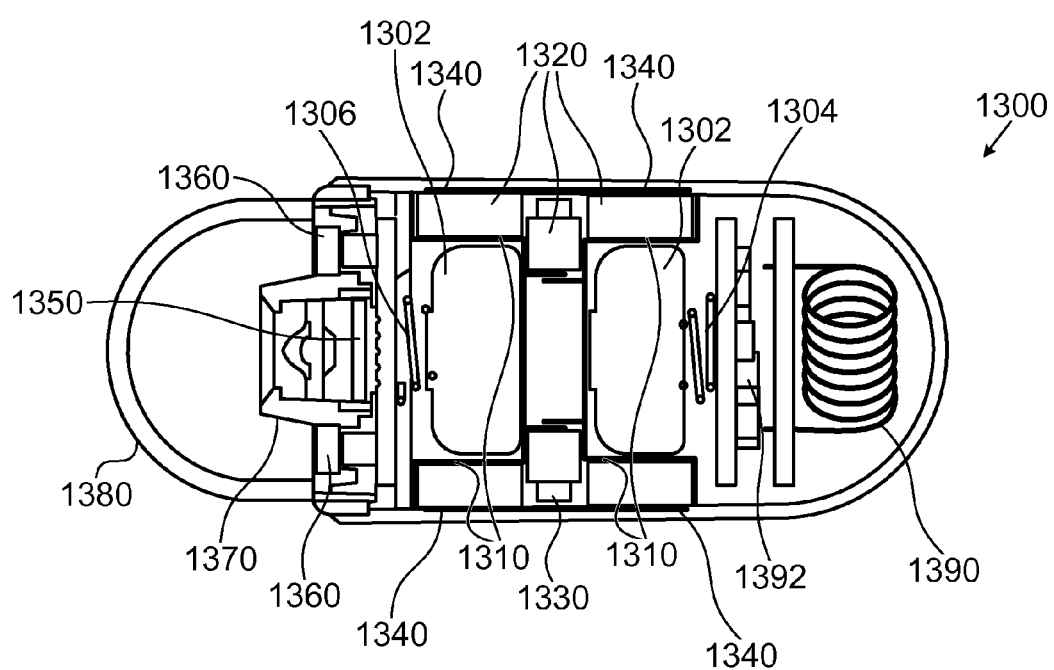
FIG. 13A shows a cross-sectional view of an in-vivo device according to an example embodiment.

FIG. 13A shows a cross-sectional view of an in-vivo capsule 1300 with a magnetic steering unit (MSU) according to an example embodiment. By way of example, the MSU of in-vivo capsule 1300 may include a magnetic carrier assembly ("MCA") 1310; permanent ring shaped magnets 1320; and sensing coils assembly (SCA) section 1340. SCA section 1340 may be identical or similar to SCA section 1250 of FIGS. 12A and 12B. FIG. 13A also shows an energy-picking coil 1330 that may be used to pick up electrical energy from an external AC magnetic field for charging batteries 1302 for powering in-vivo capsule 1300. FIG. 13A also shows an imager 1350; an illumination source 1360, which may be similar to illumination source 1270 of FIG. 12C (for example); an optical head 1370, which may be similar to optical head 1262 of FIG. 12D; an optical window 1380; a communication antenna 1390, which may be similar to communication antenna 1280 of FIG. 12B, and a transceiver circuit 1392.

Figure 13B:
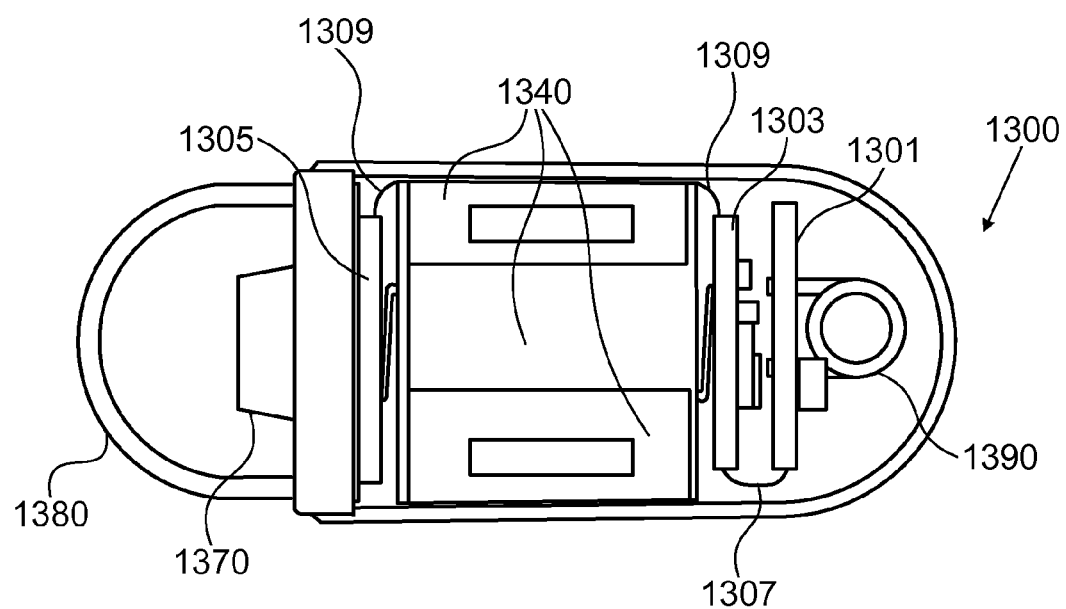
FIG. 13B shows an overall view of the in-vivo device of FIG. 13A.

FIG. 13B shows the in-vivo capsule 1100 of FIG. 13A with a multilayered imaging and sensing printed circuit board (MISP) folded according to an example embodiment. Regarding FIGS. 13A and 13B, like reference numerals refer to like elements/components/sections. The MISP of in-vivo capsule 1300 includes SCA section 1350, which is shown cylindrically folded; an imaging section that may be similar to imaging section 1240 of FIG. 12A. By way of example, the imaging section of in-vivo capsule 1300 includes PCB rigid sections 1301, 1303, 1305 (which may respectively be similar to rigid sections 1202, 1204, 1206 of FIG. 12A), and flexible/foldable sections 1307, 1309 (which may respectively be similar to sections 1296, 1294 of FIG. 12A).

Figure 14:
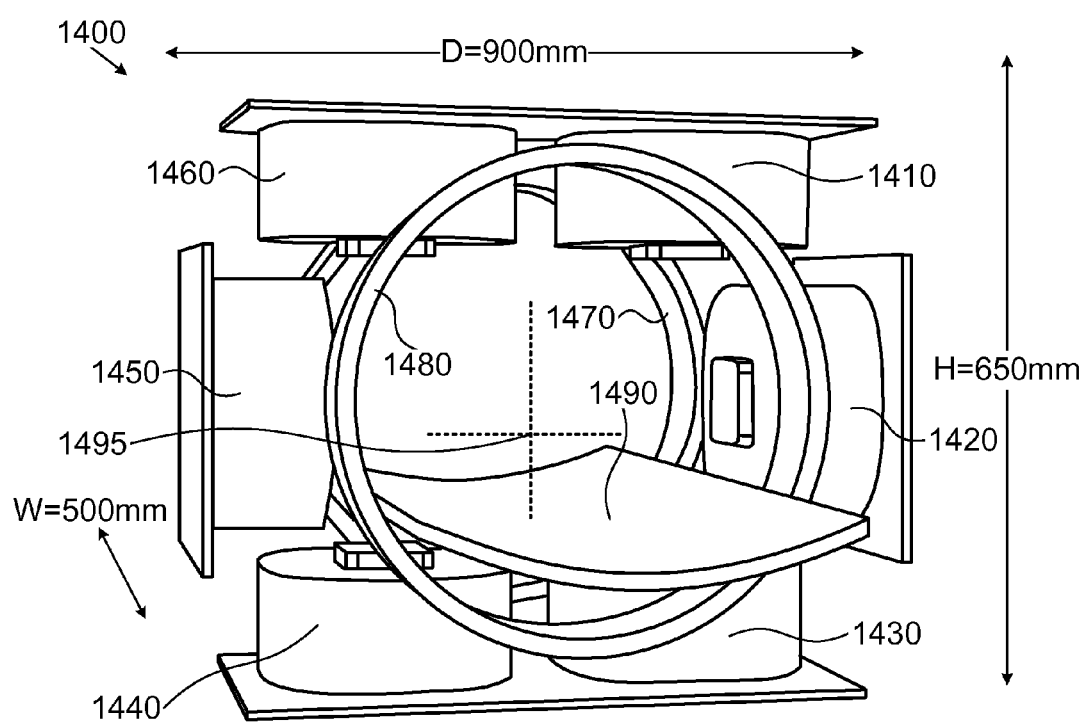
FIG. 14 illustrates an example magnetic maneuvering system for maneuvering an in-vivo device according to an example embodiment.

FIG. 14 shows an example magnetic maneuvering unit (MMU) 1400. As discussed above in connection with FIG. 1, position/orientation data may be transferred to a MMU in order for the MMU to use it as a feedback to generate a magnetic field to steer, or maneuver, an in-vivo device to a desired location and/or orientation. The MMU may include a magnetic field generator to produce the required maneuvering magnetic forces and toques, and a controller to control the operation of the magnetic field generator. By way of example, MMU 1400 may include a magnetic field generator that includes DC/AC magnetic coils 1410, 1420, 1430, 1440, 1450, 1460, 1470, and 1480. DC/AC magnetic coils 1410 through 1480 may generate DC and AC magnetic fields to produce a magnetic field vortex within the 'maneuvering space' 1495 to maneuver an in-vivo device (e.g., in-vivo device 110) swallowed by a patient lying on bed 1490. The magnetic field vortex may controllably (e.g., as a function of the feedback localization/orientation data) be moved, and its shape varied, by independently controlling the amplitude and direction of the currents flowing through the magnetic coils 1410, 1420, 1430, 1440, 1450, 1460, 1470, and 1480. Dynamic manipulation of the magnetic characteristics (e.g., location, direction, strength, orientation) of the magnetic field vortex changes the magnetic forces resulting from the interaction between the magnetic field vortex and the permanent magnets and eddy-current inducing magnets that reside in or is within the time period defined by the maneuvered in-vivo device.

FIG. 15 shows a method for timing internal sensing, by an in-vivo device, of externally generated/transmitted localization signals according to an example embodiment. An in-vivo device may operate according to a sensing time window that is defined within a work cycle of the in-vivo device. The in-vivo device may time the work cycle by using an internally generated clock signal, for example by counting pulses of a master clock signal. A reference time may be defined within the work cycle and used as a point of time from which time specifics of the sensing time window may be measured.

The in-vivo device may, during the work cycle, transmit, at step 1510, a data frame to an external receiver. The data frame may contain or include 'restoration' data to facilitate restoration, generation or production of a synchronization signal by the external receiver. Restoration, generation or production of the synchronization signal by the external receiver may be based on the clock signal, the reference time, and time specifics of the sensing time window. The in-vivo device may, during the work cycle, measure (at step 1520) time elapsing from the reference time by using the clock signal; sense (at step 1530) one or more localization signals during a time period, which is measured or calculated based on the elapsed time, that overlaps or coincides with the time specifics of the sensing time window. The one or more localization signals may be externally transmitted, for example by an external localization signals source, at times and for a duration that are specified by the synchronization signal. During the work cycle, the in-vivo device may also produce, at step 1540, localization data that represents the sensed localization signals or a processed version of the sensed localization signals. Steps 1510 to 1540 may be repeated for each work cycle or for selected work cycles.

FIG. 16 shows a method for synchronizing between sensing of localization signals by an in-vivo device and generation of the localization signals by an external localization signals source, according to an example embodiment. A receiver (e.g., data recorder) may be configured to receive a stream of data frames from an in-vivo device, for example from the in-vivo device mentioned in the discussion of FIG. 15.

During the work cycle the receiver may receive, at step 1610, a data frame from the in-vivo device. As explained in connection with FIG. 15, the in-vivo device may include in transmitted data frames restoration data to facilitate restoration of the clock signal of the in-vivo device and the reference time. The receiver may, during the work cycle, identify and extract the restoration data from the data frame, and use it, at step 1620, to restore the clock signal and the reference time. The receiver may use the restored clock signal, restored reference time and the time specifics (which are also used by the in-vivo device) to restore the sensing window (also at step 1620). The receiver may restore the sensing time window, for example, by measuring, at step 1630, by using the restored clock signal, the time elapsing from the restored reference time, and comparing the elapsed time to the time specifics of (defining) the sensing window. The elapsed times matching the time specifics of the sensing time window define the restored sensing time window.

Based on the elapsed time and time specifics of the sensing time window, the receiver may produce, at step 1640, a synchronization signal that embodies the restored sensing time window. The receiver may transfer the synchronization signal to an external localization signals source to cause it to generate one or more localization signals during a time period that overlaps or coincides with the sensing time window, for sensing the one or more localization signals by the in-vivo device during the sensing time window. Steps 1610 to 1640 may be repeated for each work cycle or for selected work cycles of the in-vivo device, or for each data frame, or for selected data frames, that is/are received by the data recorder.

FIG. 17 shows a method for synchronizing generation of a localization signal to sensing of the localization signal in an in-vivo device according to an example embodiment. The synchronization method may include predefining, at step 1710, for an in-vivo device, a sensing time window during which the in-vivo device may internally sense a localization signal originating from a localization signals source external to the in-vivo device; intermittently transmitting, at step 1720, by the in-vivo device, data to an external receiver (e.g., data recorder); restoring, at step 1730, by the receiver, the sensing time window from data transmitted by the in-vivo device; producing, at step 1740, by the receiver, based on the restored sensing time window, a synchronization signal corresponding to the restored sensing time window, in order to signal the sensing time window to the localization signals source; transferring, at step 1750, the synchronization signal to the localization signals source; and producing, at step 1760, by the localization signals source, and concurrently sensing by the in-vivo device, a localization signal during the sensing time window. Steps 1710 to 1760 may be repeated for each work cycle or for selected work cycles of the in-vivo device, or for each data frame or for selected data frames, that is/are received by the data recorder.

The articles "a" and "an" are used herein to refer to one or to more than one (i.e., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. For example, a system may include a non-transitory storage medium such as storage unit 240, computer-executable instructions such as timing unit 114 and a controller such as controller 260. Some embodiments may be provided in a computer program product that may include a non-transitory machine-readable medium, having stored thereon instructions, which may be used to program a computer, or other programmable devices, to perform methods as disclosed above.

Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of in-vivo devices (e.g., in-vivo devices with one or more imagers, in-vivo devices with no imagers at all, etc.), and to various types of receivers. Hence the scope of the claims that follow is not limited by the disclosure herein.

The invention claimed is:

1. A method for timing sensing of localization signals by an in-vivo device, the method comprising:
   by an in-vivo device operating according to a sensing time window within a work cycle of the in-vivo device, the in-vivo device timing the work cycle using a clock signal and having defined within the work cycle a reference time, performing during the work cycle:
   (i) transmitting a data frame to a receiver, the data frame comprising data facilitating generation by the receiver of a synchronization signal for an external localization signals source based on a clock pulse, the reference time, and on time specifics of the sensing time window;
   (ii) measuring time elapsing from the reference time by using the clock signal;
   (iii) sensing, based on the elapsed time, during a time period complying with the time specifics of the sensing time window, one or more localization signals externally transmitted by the external localization signals source at times and for duration specified by the synchronization signal; and
   producing localization data representative of the sensed externally transmitted localization signals.

2. The method as in claim 1, wherein the sensing time window and/or the reference time are within the time period of a transmission period of the work cycle during which the data frame is transmitted, or within the time period of an idle period of the work cycle during which the in-vivo device refrains from transmitting data.

3. The method as in claim 1, wherein measuring the time elapsing from the reference time comprises counting clock pulses of the clock signal, by a clock counter, relative to an initial count value.

4. The method as in claim 3, comprising resetting the clock counter during each work cycle or during selected work cycles.

5. The method as in claim 3, comprising initializing the clock counter to an initial value at a time overlapping with the reference time.

6. The method as in claim 3, wherein the one or more localization signals are generated by the external localization signals source based on the restored clock signal and based on restored data indicative of the reference time.

7. The method as in claim 1, wherein the data indicative of the reference time is any one of: prefix data of the data frame, suffix data of the data frame, data indicative of start-of-transmission of the data frame, data indicative of end-of-transmission of the data frame, a group of data bits in the data frame, and a data bit in the data frame.

8. The method as in claim 1, comprising:
   entering a sensing mode when a first time elapses from the reference time, to enable sensing the one or more externally transmitted localization signals during the sensing time window; and
   exiting the sensing mode when a second time elapses relative to the reference time.

9. The method as in claim 8, wherein measuring time specifics of the sensing time window and sensing time sub-windows comprises counting clock pulses of the clock signal.

10. The method as in claim 8, further comprising adjusting the time specifics contingent on a rate at which data frames are transmitted, to adjust the sensing time window or the sensing time sub-window.

11. The method as in claim 1, wherein each localization signal is associated with a particular coordinate of a coordinate system.

12. The method as in claim 1, wherein the sensing time window comprises one or more sensing time sub-windows to facilitate sensing one or more localization signals respectively associated with one or more coordinates, and comprising measuring time specifics of the sensing time window and time specifics of each of the sensing time sub-windows relative to the reference time.

13. The method as in claim 12, wherein adjusting the time specifics comprises adjusting a number of clock pulses of the clock signal relative to the reference time.

14. The method as in claim 13, further comprising transmitting the adjusted number of cycles of the localization signal to the external localization signals source.

15. The method as in claim 12, further comprising transmitting the adjusted time specifics to the in-vivo device or to the receiver.

16. The method as in claim 12, comprising adjusting any one of a number of cycles of a localization signal and a frequency of a localization signal in response to an adjustment of the sensing time window or sensing time sub-window.

17. An in-vivo device capable of timing sensing of externally generated localization signals, comprising:
   a timing mechanism having a clock generator to generate a clock signal to time a work cycle of the in-vivo device, within the work cycle is defined a reference time;
   a transmitter to transmit, within the work cycle, a data frame to a receiver, the data frame comprising data facilitating restoration, by the receiver, of the clock signal and the reference time;
   a memory for storing time specifics of a sensing time window defined within the work cycle;
   a sensing coils assembly to sense externally generated localization signals;
   a controller operably coupled to the timing mechanism, transmitter, memory and sensing coils assembly, wherein the controller is configured, within the work cycle, to:

measure time elapsing from the reference time by using the clock signal, and, based on the elapsed time and time specifics, operate the sensing coils assembly to sense an externally generated localization signal during a time period overlapping with the sensing time window; and transmit, using the transmitter, data representative of the sensed externally generated localization signal.

18. The in-vivo device as in claim 17, wherein the controller is further configured to change the time specifics contingent on a rate at which the controller is transmitting data frames using the transmitter.

19. A data recorder for synchronizing between an in-vivo device and a localization system, the data recorder comprising:

a memory for storing time specifics, the time specifics defining a sensing time window within a work cycle of an in-vivo device during which the in-vivo device operates a sensing coils assembly to sense one or more localization signals;

a receiving unit to receive a data frame from the in-vivo device, the data frame comprising a clock signal and a reference time originating from the in-vivo device;

a time restoration unit configured to use one or more data bits in the data frame, to restore the clock signal and reference time from the received data frame; and a synchronization signal generator operationally coupled to the receiving unit and time restoration unit, and configured to cause, based on the restored clock signal, restored time reference, and stored time specifics of the sensing time window, an external localization signals source to generate a localization signal during a time period overlapping with the sensing time window, for sensing the externally generated localization signal by the in-vivo device during the sensing time window.

20. The data recorder receiver as in claim 19, wherein the time specifics are adjustable contingent on a rate at which the receiving unit receives data frames from the in-vivo device, to adjust the sensing time window.

* * * * *